(12) United States Patent
Alving et al.

(10) Patent No.: US 7,270,964 B2
(45) Date of Patent: Sep. 18, 2007

(54) DETECTION OF ANTIBODIES TO SQUALENE IN SERUM

(75) Inventors: Carl R Alving, Bethesda, MD (US); Gary R Matyas, Olney, MD (US); Nabila M Wassef, Potomac, MD (US); Mangala Rao, Silver Spring, MD (US)

(73) Assignee: United States of America as Represented by the Secretary of the Army, Washington, DC (US)

( * ) Notice: Subject to any disclaimer, the term of this patent is extended or adjusted under 35 U.S.C. 154(b) by 429 days.

(21) Appl. No.: 10/886,561

(22) Filed: Jul. 9, 2004

(65) Prior Publication Data

US 2004/0248224 A1 Dec. 9, 2004

Related U.S. Application Data

(62) Division of application No. 09/859,389, filed on May 18, 2001, now Pat. No. 6,900,025.

(60) Provisional application No. 60/205,041, filed on May 18, 2000.

(51) Int. Cl.
*G01N 33/53* (2006.01)

(52) U.S. Cl. ............ 435/7.1; 435/7.92; 435/7.95; 530/387.1; 436/514

(58) Field of Classification Search ........... 435/7.1, 435/7.92, 7.95; 530/387.1; 436/514
See application file for complete search history.

(56) References Cited

U.S. PATENT DOCUMENTS

| | | | |
|---|---|---|---|
| 5,419,904 A | 5/1995 | Irie | |
| 5,419,921 A | 5/1995 | Molacek et al. | |
| 5,709,879 A | 1/1998 | Barchfeld et al. | |
| 6,166,050 A | 12/2000 | Lombardo et al. | |
| 6,191,108 B1 | 2/2001 | Rodkey et al. | |
| 6,214,566 B1 | 4/2001 | Asa et al. | |

FOREIGN PATENT DOCUMENTS

| | | |
|---|---|---|
| WO | WO95/00146 A1 | 1/1995 |
| WO | WO98/20137 A1 | 5/1998 |

OTHER PUBLICATIONS

Chan et al. (GAO Gulf War Illness report 1999, Mar. released).*
Tenebaum et al. (Lancet 1997 vol. 349, p. 449-54).*
Fung et al., "3, 4-dicarboxylic Acid (A-87049): A Novel Potent Squalene Synthase Inhibitor," Journal of Medicinal Chemistry. 1997, vol. 40, No. 14, pp. 2123-2125.
Hanley et al., "Solubilization, Partial Purification, and Immunodetection of Squalene Synthetase from Tobacco Cell Suspension Cultures," Plant Physiology, 1992, vol. 98, No. 1, pp. 215-220.
Ryder, N.S. et al, "Interaction of terbinafine with human serum and serum proteins," Journal of Medical and Veterinary Mycology, 1992, vol. 30, pp. 451-460.

Aggarwal, B.B. et al., "Human Lymphotoxin: Production by a Lymphoblastoid Cell Line, Purification, and Initial Characterization", Journal of Biological Chemistry, 1984, vol. 259, No. 1, pp. 686-691.
Alving, C.R., "Natural Antibodies Against Phospholipids and Liposomes in Humans", Biochem. Society Transactions, 1984, vol. 12, No. 2, pp. 342-344.
Alving, C.R. et al., "Naturally Occurring Autoantibodies to Cholesterol in Humans", Biochemical Society Transactions, 1989, vol. 17, No. 4, pp. 637-639.
Alving, C.R. et al., "Preparation and Use of Liposomes in Immunological Studies". In: G. Gregoriadis (Ed.) Liposome Technology, vol. 3 (Second Ed.), CRC Press, Inc. Boca Raton, 1993, pp. 317-343.
Alving, C.R. et al., "Antibodies to Cholesterol, Cholesterol Conjugates, and Liposomes: Implications for Atherosclerosis and Autoimmunity", Critical Review in Immunology, 1991, vol. 10, No. 5, pp. 441-453.
Alving, C.R. et al., "Naturally Occurring Antibodies to Cholesterol: A New Theory of LDL Cholesterol Metabolism", Immunology Today, 1999, vol. 20, No. 8, pp. 362-366.
Alving, C.R. et al., "Antibodies to Cholesterol: Biological Implications of Antibodies to Lipids", Current Topics Microbiology Immunology, 1996, vol. 210, pp. 181-186.
Alving et al., "Immunization with Cholesterol-Rich Liposomes Induces Anti-Cholesterol Antibodies and Reduces Diet-Induced Hypercholesterolemia and Plaque Formation", J. Lab. Clin. Med., 1996, vol. 127, No. 1, pp. 40-49.
Alving, C.R. et al., Letters to the Editor, Exp. Mol. Pathol., 2000, vol. 68, pp. 196-198.
Asa, P. et al., "Antibodies to Squalene in Gulf War Syndrome", Exp. Mol. Pathol., 2000, vol. 68, No. 1, pp. 55-64.
Asa, P.B. et al., "Antibodies to Squalene in Recipients of Anthrax Vaccine", Exp. Mol. Pathol., 2002, vol. 73, No. 1, pp. 19-27.
Aniagolu, J. et al., "Analysis of Anticholesterol Antibodies Using Hydrophobic Membranes", J. Immunol. Meth., 1995, vol. 182, No. 1, pp. 85-92.
Banerji, B. et al, "Anti-Liposome Antibodies Induced By Lipid A. I. Influences of Ceramide, Glycosphingolipids, and Phosphocholine on Complement Damage", J. Immunol., 1981, vol. 126, No. 3, pp. 1080-1084.
Beaumont, V. et al., "Antiestrogen Antibodies, Oral Contraception and Systemic Lupus Erythematosus", Clin. Physiol. Biochem., 1989, vol. 7, pp. 263-368.
Brochu, M. et al., "Monoclonal Antibodies for Use With 125-Iodine-Labeled Radioligands in Progesterone Radioimmunoassay", J. Steroid Biochem., 1984, vol. 21, No. 4, pp. 405-411.
Bucala, R. et al., "Anti-oestrogen Antibodies in Users of Oral Contraceptives and in Patients with Systemic Lupus Erythamatosus", Clin. Exp. Immunol., 1987, vol. 67, No. 1, pp. 167-175.

(Continued)

*Primary Examiner*—Long V. Le
*Assistant Examiner*—Jacob Cheu
(74) *Attorney, Agent, or Firm*—Elizabeth Arwine

(57) ABSTRACT

The invention is a method for detecting squalene in sera.

6 Claims, 20 Drawing Sheets

OTHER PUBLICATIONS

Figure 1:
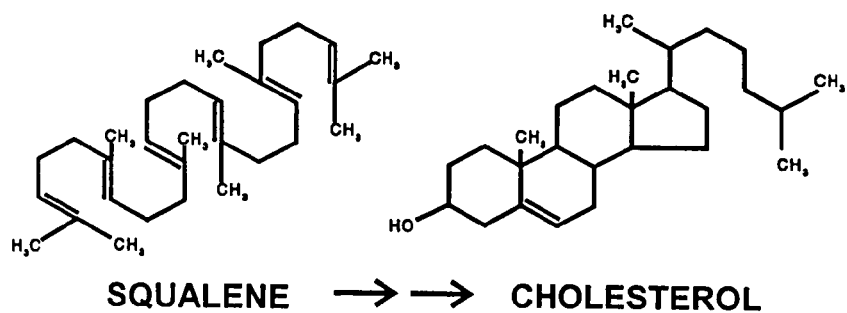

Counihan, K.A., et al., "Anti-estrogen Antibodies in Systemic Lupus Erythematosus: A Quantitative Evaluation of Serum Levels", Immuno. Invest., 1991, vol. 20, No. 3, pp. 317-331.

Cunningham, C.K. et al., "Safety of 2 Recombinant Human Immunodeficiency Virus Type 1 (HIV-1) Envelope Vaccines in Neonates born to HIV-1-Infected Women", Clin. Infect. Dis., 2001, vol. 32, No. 5, pp. 801-807.

Dijkstra, J. et al., "Interaction of Anti-Cholesterol Antibodies with Human Lipoproteins", J. Immunol., 1996, vol. 157, No. 5, pp. 2006-2013.

Dörsam, H. "Antibodies to Steroids From A Small Human Naive IgM Library", FEBS Lett., 1997, vol. 414, No. 1, pp. 7-13.

Drulak, M.W. et al., "Vaccination of Serpositive Subjects With CHIRON CMV gB Subunit Vaccine Combined With MF59 Adjuvant for Production of CMV Immune Globulin", Viral Immunol., 2000, vol. 13, No. 1, pp. 49-56.

Fahey, J.L. et al., "Proliferation and Differentiation of Lymphoid Cells: Studies With Human Lymphoid Cell Lines and Immunoglobulin Synthesis", Ann. N.Y. Acad. Sci., 1971, vol. 190, pp. 221-234.

Fantl, V.E. et al., Simultaneous Production of Monoclonal Antibodies to Dehydroepiandresterone, Oestradiol, Progesterone and Testosterone, J. Endocrinol., 1984, vol. 100, No. 3, pp. 367-376.

Franek, M., "Structural Aspects of Steroid-Antibody Specificity", J. Steroid Biochem., 1987, vol. 28, No. 1, pp. 95-108.

Fulco, C.E., et al., "Gulf War and Health: Depleted Uranium, Pyridostigmine Bromide, Sarin, Vaccines", National Academy Press, Washington, DC, 2000, vol. 1, p. 307.

Galfré, G. et al., "Preparation of Monoclonal Antibodies: Strategies and Procedures", Methods Enzymol., 1981, vol. 73, (Pt.B), pp. 3-46.

Gasparini, R. et al., "Increased Immunogenicity of the MF-59-adjuvanted Influenza Vaccine Compared to a Conventional Subunit Vaccine in Elderly Subjects", Eur. J. Epidemiol., 2001, vol. 17, No. 2, pp. 135-140.

Gigliotti, F., et al., "Reproducible Production of Protective Human Monoclonal Antibodies by Fusion of Peripheral Blood Lymphocytes with A Mouse Myeloma Cell Line", J. Infect. Dis., 1984, vol. 149, No. 1, pp. 43-47.

Granner, D.K., "Hormones of the Adrenal Cortex", In: R.K. Murray, et al. (Eds.) Harper's Biochemistry, 24th Edition, Appleton & Lang, Stamsord, p. 547-559

Grover, P.K. et al., "Specificity of Antisera to Sex Steroids I—The Effect of Substitution and Sterochemistry", J. Steroid Biochem., 1977, vol. 8, No. 2, pp. 121-126.

Gupta, R.K. et al., "Adjuvant Properties of Non-Phospholipid Liposomes (Novasomes®) in Experimental Animals for Human Vaccine Antigens", Vaccine, 1996, vol. 14, No. 3, pp. 219-225.

Harro, C.D. et al., "Safety and Immunogenicity Trial in Adult Volunteers of Human Papillomavirus 16 L1 Virus-Like Particle Vaccine", J. Natl. Cancer Inst., 2001, vol. 93, No. 4, pp. 284-292.

Heineman, T.C. et al., "A Randomized, Controlled Study in Adults of the Immunogenicity of A Novel Hepatitis B Vaccine Containing MF59 Adjuvant", Vaccine, 1999, vol. 17, No. 22, pp. 2769-2778.

Kahn, J.O. et al., "Clinical and Immunologic Responses to Human Immunodeficiency Virus (HIV) Type $1_{SF2}$ gp120 Subunit Vaccine Combined With MF59 Adjuvant With or Without Muramyl Tripeptide Dipalmitoyl Phosphatidylethanolamine in Non-HIV-Infected Human Volunteers", J. Infect. Dis., 1994, vol. 170, No. 5, pp. 1288-1291.

Kester, K.E. et al., "Efficacy of Recombinant Circumsporozite Protein Vaccine Regimens Against Experimental *Plasmodium falciparum* Malaria", J. Infect. Dis., 2001, vol. 183, No. 4, pp. 640-647.

Köhler, G. et al., "Continuous Cultures of Fused Cells Secreting Antibody of Predefined Specificity", Nature, 1975, vol. 256, No. 5517, pp. 495-497.

Koivisto, P.V. et al., "Increased Amounts of Cholesterol Precursors in Lipoproteins After Ileal Exclusion", Lipids, 1988, vol. 23, No. 10, pp. 993-996.

Kuwahara, A. et al., "Autoantibody Against Testosterone In A Woman With Hypergonadotropic Hypogonadism", J. Clin. Endocrin. Metab., 1998, vol. 83, No. 1, pp. 14-16.

Lohner, K. et al., "Squalene Promotes The Formation of Non-Bilayer Structures in Phospholipid Model Membranes", Biochem. Biophys. Acta., 1993, vol. 1152, No. 1, pp. 69-77.

Mais, D.E. et al., "Specific Interactions of Progestins and Anti-Progestins with Progesterone Antibodies, Plasma Binding Proteins and the Human Recombinant Receptor", J. Steroid Biochem. Molec. Biol., 1995, vol. 54, Nos. 1/2, pp. 63-69.

Matyas, G.R. et al., "Induction and Detection of Antibodies to Squalene", *J. Immunol. Methods*, 2000, vol. 245, Nos. 1/2, pp. 1-14.

Matyas, G.R. et al., "Induction and Detection of Antibodies to Squalene II. Optimization of the Assay for Murine Antibodies", *J. Immunol. Methods*, 2002, vol. 267, No. 2, pp. 119-129.

Mayes, P.A., "Cholesterol Synthesis, Transport, & Excretion", *Harper's Biochemistry*, 24th Edition, Appleton & Lang, Stamford, 1996, p. 271-283.

McFarland, E.J. et al., "Human Immunodeficiency Virus Type 1 (HIV-1) gp120-Specific Antibodies in Neonates Receiving an HIV-1 Recombinant gp120 Vaccine", Concise Comm., 2001, vol. 184, No. 10, pp. 1331-1335.

Miettinen, T.A., "Diurnal Variation of Cholesterol Precursors Squalene and Methyl Sterols in Human Plasma Lipoproteins", J. Lipid Res., 1982, vol. 23, No. 3, pp. 466-473.

Minutello, M. et al., "Safety and Immunogenicity of an Inactivated Subunit Influenza Virus Vaccine Combined With MF59 Adjuvant Emulsion in Elderly Subjects, Immunized for Three Consecutive Influenza Seasons", Vaccine, 1999, vol. 17, No. 2, pp. 99-104.

Mitchell, D.K. et al., "Immunogenicity of a Recombinant Human Cytomegalovirus gB Vaccine in Seronegative Toddlers", J. Pediatr. Infect. Dis., 2002, vol. 21, No. 2, pp. 133-138.

Moinuddin, A.A., "Binding of Naturally Occurring Anti-DNA Antibodies To Estradiol", Biochem. Mol. Biol. Int., 1998, vol. 45, No. 3, pp. 511-518.

Newhook, R. et al., "Exposure To Styrene in the General Canadian Population", IARC Sci. Pub., 1993, vol. 127, pp. 27-33.

Nicholson, K.G. et al., "Safety and Antigenicity of Non-Adjuvanted and MF59-Adjuvanted Influenza A/Duck/Signapore/97 (H5N3) Vaccine: A Randomized Trial of Two Potential Vaccines Against H5N1 Influenza", Lancet, 2001, vol. 357, No. 9272, pp. 1937-1943.

Ott, G. et al., "The Adjuvant MF59: A 10-Year Perspective", *Meth. Mol. Med.*, Humana Press, 2000, vol. 42, pp. 211-228.

Pinto, M. et al., "Anti-Steroid Factor/s in Normal and Pathological Human Sera", Vox Sang, 1970, vol. 18, No. 2, pp. 155-162.

Pittman, P.R. et al., "Anthrax Vaccine: Short-term Safety Experience in Humans", Vaccine, 2002, vol. 20, Nos. 5-6, pp. 972-978.

Podda, A., "The Adjuvanted Influenza Vaccines With Novel Adjuvants: Experience With The MF59-Adjuvanted Vaccine", Vaccine, 2001, vol. 19, Nos. 17-19, pp. 2673-2680.

Relas, H. et al., "Fate of Intravenously Administered Squalene and Plant Sterols in Huamn Subjects", J. Lipid Res., 2001, vol. 42, No. 6, pp. 988-994.

Rickman, L.S. et al., "Use of Adjuvant Containing Mycobacterial Cell-Wall Skeleton, Monophosphoryl Lipid A., and Squalene in Malaria Circumsporozoite Protein Vaccine", Lancet, 1991, vol. 337, No. 8748, pp. 998-1001.

Schuster, B. et al., "Production of Antibodies Against Phosphocholine, Phosphatidylcholine, Sphingomyelin, and Lipid A By Injection of Liposomes Containing Lipid A", J. Immunol., 1979, vol. 122, No. 3, pp. 900-905.

Spanggord, R.J. et al., "Development and Application of an Analytical Method for the Determination of Squalene in Formulations of Anthrax Vaccine Adsorbed", J. Pharm. Biomed. Anal., 2002, vol. 29. No. 1-2, pp. 183-193.

Stewart, M.E., "Sebaceous Gland Lipids", Semin Dermatol., 1992, vol. 11, No. 2, pp. 100-105.

Stollar, B.D. et al., "Cross-Reactions of Nucleic Acids With Monoclonal Antibodies to Phosphatidylinositol Phosphate and Cholesterol", Mol. Immunol., 1989, vol. 26, No. 1, pp. 73-79.

Stoute, J.A. et al., "A Preliminary Evaluation of A Recombinant Circumsporozoite Protein Vaccine Against *Plasmodium falciparum* Malaria", New Engl. J. Med., 1997, vol. 336, No. 2, pp. 86-91.

Stoute, J.A. et al., "Long-Term Efficacy and Immune Responses Following Immunization With The RTS,S Malaria Vaccine", J. Infect. Dis., 1998, vol. 178, No. 4, pp. 1139-1144.

Swartz, Jr. G.M. et al., "Antibodies To Cholesterol", Proc. Natl. Acad. Sci. U.S.A., 1988, vol. 85, No. 6, pp. 1902-1906.

Teng, N.N.H. et al., "Protection Against Gram-Negative Bacteremia and Endotoxemia With Human Monoclonal IgM Antibodies", Proc. Natl. Acad. Sci. U.S.A., 1985, vol. 82, No. 6, pp. 1790-1794.

Wassef, N.M. et al., "Phosphate Binding Specificities of Monoclonal Antibodies Against Phosphoinositides in Liposomes", 1984, vol. 21, No. 10, pp. 863-868.

* cited by examiner

SQUALENE →→ CHOLESTEROL

DETECTION OF ANTIBODIES TO SQUALENE IN SERUM

This application is a divisional of application Ser. No. 09/859,389 filed May 18, 2001 now U.S. Pat. No. 6,900,025, which claims the benefit of Provisional Application Ser. No. 60/205,041 filed May 18, 2000.

I. STATEMENT REGARDING FEDERALLY SPONSORED RESEARCH

Not applicable.

II. FIELD OF THE INVENTION

Squalene (SQE) is a triterpenoid hydrocarbon oil, $C_{30}H_{50}$, that is widely produced by both plants and animals, and is present in human food. SQU is also widely used in skin cosmetics. In humans, SQE serves a as precursor in the synthesis of cholesterol and all of the steroid hormones (Mayes, 1996; Granner, 1996) (FIG. 1). Both SQE and cholesterol are transported in the blood on very low density lipoproteins (VLDL) and low density lipoproteins (LDL) (Miettinen, 1982; Koivisto and Miettinen, 1988). Squalene and cholesterol are also synthesized in the liver and in the epidermis of the skin where SQE comprises a large amount of the oil secreted by sebaceous glands (Stewart, 1992). Because it is a naturally-occurring biodegradable oil, SQE and its hydrogenated derivative squalane (SQA) have each been proposed for use as the oil component of oil-in-water (o/w) emulsions for new generations of adjuvants for vaccines (Minutello et al., 1999).

Immunization against a potential antigen such as SQE presents a particular Catch-22 challenge: first, there have never been any previous antibodies developed that could serve as validated positive controls for anti-SQE antibodies, and second, there is no validated assay available for detecting antibodies to SQE. To overcome this difficult dilemma in the present study, the horns of which are the simultaneous lack of positive antibody controls from immunized animals and lack of a validated assay for antibodies to SQE, our first goal was to inject SQE into mice to try to create antibodies that could potentially be validated as having anti-SQE activity. The second goal, namely the creation of monoclonal antibodies that could serve as positive antibody controls, was considered to be a requirement in the ultimate third goal of development of a valid immunoassay for detection of specific antibodies to SQE.

It has been previously reported that SQE incorporated into non-phospholipid liposomes has an adjuvant effect on the induction of antibodies to a non-phospholipid liposomal protein, but the adjuvant effect was not enhanced further by simultaneous incorporation of lipid A (Gupta et al., 1996). Although incorporation of lipid A without SQE into non-phospholipid liposomes was not tested in the latter study, the potent adjuvant effect of liposomal SQE for liposomal protein was clearly shown. This adjuvant effect of liposomal SQE therefore may also have played a role in our liposomes in the induction of antibodies to SQE.

As with 71% cholesterol in liposomes, the biophysical conformation of 71% SQE in our liposomes is not completely clear. Previous work has suggested that SQE locates itself in the most disordered region of liposomes, predominately in the center area of the liposomal bilayer (Lohner et al., 1993). Because of this it has been proposed that SQE adopts a coil rather than an extended conformation when it is located in the bilayer interior. Although relatively small amounts of SQE have a disruptive effect on the liposomal bilayer and lead to formation of tubules having the $H_{II}$ conformation in liposomes containing phosphatidylethanolamine (Lohner et al., 1993), the $H_{II}$ conformation does not occur in liposomes, such as ours, that lack phosphatidylethanolamine. Nonetheless, the reported ability of SQE to lower the transition temperature of phosphatidylcholine and to cause disruption in the stability of the liposomal bilayer (Lohner et al., 1993), together with the high concentrations of SQE combined with lipid A in the liposomes used in this study, may play a role in the potent ability of these liposomes to induce antibodies to SQE.

From a purely structural standpoint, it may not be initially surprising that antibodies to SQE can be induced in a similar manner to those against cholesterol, in view of the striking apparent structural similarity of SQE and cholesterol (FIG. 1). Balanced against this, however, is the observation that the immunogenic epitope of liposome-associated cholesterol is the polar 3-β-hydroxy group in the A ring (Dijkstra et al, 1996), and the fact that SQE not only lacks any closed ring, but is an exceedingly hydrophobic alkene that completely lacks any polar group.

What, if any, are the potential consequences of induction of antibodies to SQE? A recent publication claims to have detected antibodies to SQE in sick but not in healthy individuals (Asa et al., 2000). However, we believe that such a conclusion may be premature, based on a technical critique of the reported Western blot-type assay that was used (Alving and Grabenstein, 2000). Turning again to cholesterol for comparison, SQE, as a precursor in the synthesis of cholesterol, is found nearly everywhere that cholesterol is found, with the apparent exception that SQE probably does not have a structural role in promoting the stability of membranes. As with cholesterol, SQE circulates in the blood as a constituent of LDL and VLDL (Miettinen, 1982; Koivisto and Miettinen, 1988). Naturally-occurring antibodies to cholesterol have been demonstrated to be present in virtually all human serum samples tested, and they have been proposed to have a vital beneficial role in the normal regulation of LDL and VLDL metabolism (Alving and Wassef, 1999).

III. BACKGROUND OF THE INVENTION

Antibodies to SQE have had great interest in the popular press. Asa et al., described antibodies to SQE in the serum of sick Gulf War Veterans and purported that these antibodies were responsible for their disease [Asa, et al., "Antibodies to Squalene in Gulf War Syndrome," Exp. Mol. Path. 68:55 (2000)]. Asa's assay has been criticized for technical reasons, which render the reported results as highly questionable or invalid [Alving, et al., Letter to the Editor. Exp. Mol. Path. 68:196 (2000)]. U.S. Pat. No. 6,214,566 (Asa, et al.) discloses an immunoassay for detecting anti-squalene antibodies.

In order to develop a highly reliable assay for antibodies to SQE, we developed murine monoclonal antibodies to SQE to serve as positive controls [Matyas, et al., "Induction and detection of antibodies to squalene," J. Immunol. Meth. 245:1 (2000)]. These monoclonal were used to develop an assay for measuring antibodies to squalene in human serum.

IV. SUMMARY OF THE INVENTION

In view of the success that was previously found using lipid A as an adjuvant for inducing antibodies to cholesterol (Swartz et al., 1988; Alving and Swartz, 1991), immunization strategies using SQE combined with lipid A were employed in attempting to induce antibodies to SQE. The results demonstrate that murine antibodies to SQE can be induced by injection of SQE-loaded liposomes containing lipid A, and the antibodies can be detected by an ELISA in which the antigen is coated on hydrophobic membranes instead of polystyrene microtiter wells. This has allowed creation of an immunoassay for demonstrating that mAbs to SQE can be produced that differentiate SQE from SQA.

The assay used in the development of the monoclonal antibodies to SQE used 96 well plates containing PVDF membranes. This assay was highly reproducible, but was very labor intensive; limiting the number of samples that could be assayed. Studies with different lots of plates revealed variations in assay results (data not shown). In addition, the assay used PBS-4% fetal bovine serum (FBS) as a blocker/dilutent buffer. Like human serum, FBS undoubtedly contains SQE. This serum SQE could potentially compete for antibody binding in the assay. In order to overcome these shortcomings, we describe a modified, highly reproducible assay for antibodies to SQE.

A new highly reproducible and high through-put assay for measuring antibodies to SQE was developed. The assay utilizes Costar 96 well U bottom sterile tissue culture plates, which are not routinely used for ELISA assay. None of the standard ELISA plates tested were useful for this assay; most gave high background.

The accompanying drawings show illustrative embodiments of the invention from which these and other of the objectives, novel features and advantages will be readily apparent.

V. DESCRIPTION OF THE DRAWINGS

FIG. 1 shows the structure of squalene and cholesterol.

FIG. 2 shows the binding activity of mouse serum IgM to SQE by ELISA. Mice were immunized biweekly with: A) Liposomes containing lipid A as an adjuvant and composed of DMPC/DMPG/SQE in a molar ratio of 9:1:2.5 (group 4); or B) an emulsion containing of 20% SQE, 5% Tween 80, 5% Span 85 and lipid A (group 6); or C) the above liposomes containing lipid A as an additional adjuvant. Serum obtained from these mice were tested by ELISA as described in the Materials and Methods. Polystyrene "U" bottom plates were coated with 10 μg/well of SQE in ethanol. Binding activity of the indicated dilutions of preimmune and immune serum was assayed at the indicated time points. Results are presented as the mean absorbance from triplicate wells containing squalene subtracted from the absorbance of triplicate wells lacking squalene±SD.

FIG. 3 shows the end point dilution IgM titers of immune mouse serum against SQE, and liposomes containing or lacking SQE. Serum from mice immunized biweekly with liposomes containing lipid A as an additional adjuvant and composed of DMPC/DMPG/SQE in a molar ratio of 9:1:2.5 (group 4) were tested by ELISA. Capture antigens for the assay consisted of SQE or of liposomes containing or lacking squalene. Polystyrene "U" bottom plates were coated with 10 μg/well of SQE in ethanol, or with the equivalent amount of L(SQE), or with the equivalent amount of L. The results shown were obtained by subtracting the absorbance of triplicate wells containing the appropriate capture antigen from the absorbance of triplicate wells lacking antigens. Endpoint IgM antibody titers were calculated from the highest dilution of serum giving twice the absorbance of the background.

FIG. 4 shows the comparative binding of a mAb to SQE or SQA coated on PVDF or PS flat bottom plates. Each well contained 10 μg of SQA or SQE dissolved in 0.1 ml of isopropanol, or isopropanol alone (control), as appropriate, at the concentrations indicated. The culture supernatant of a mAb was diluted in PBS-4% fetal bovine serum (PVDF plates) or PBS-0.3% gelatin (PS plates). ELISAs were performed as described in the Methods section for the PVDF and PS plates, respectively. Similar results were observed with 8 other clones. Values are the mean±standard deviation of triplicate wells.

FIG. 5 shows the specific binding of mAb clone 5 to SQE, but not SQA. The assay was conducted with PVDF plates as described in the legend to FIG. 4.

FIG. 6 shows the binding of mAb clone 15 to SQE and cross-reactivity with SQA. The assay was conducted with PVDF plates as described in the legend to FIG. 4.

FIG. 7 shows the reactivity of monoclonal antibodies to liposomes containing or lacking SQE or SQA. L(SQE), L(SQA) and L (33 nmol of phospholipid) in 0.05 ml of PBS was placed in each well of a PS"U" bottom plate. The plates were processed as described in the Methods. Culture supernatants from the indicated clones were diluted in PBS-0.3% gelatin and 0.05 ml was placed in each well. Values are the mean±standard deviation of triplicate wells. A, B, C, D: Binding of the indicated culture supernatants to L(SQE), L(SQA), and L. E: Negative controls consisting of binding of an irrelevant IgM secreting clone 2D4 (IgM anti-$G_{M2}$).

FIG. 8 shows the binding of antiserum IgM to SQE and SQA on PVDF and PS flat bottom ELISA plates. Pre-immune or 3 day post-immune serum from mice immunized with liposomes containing 71% SQE was diluted in PBS-4% fetal bovine serum (PVDF plates) or PBS-0.3% gelatin (PS plates). ELISAs were performed as described in the Methods section for the PVDF and PS plates, respectively. Values are the mean±standard deviation of triplicate wells.

FIG. 9 shows the comparison of plates from different manufacturers with PBS-4% FBS as a blocker/diluent. Plates were coated with 100 nmol of SQE. mAbs SQE #16 and SQE #18 were diluted 1:10. The normal mouse serum and anti-SQE serum were diluted 1:50. The ELISA was performed as described for the standard protocol using PBS-4% FBS. Values are the mean of triplicate determination±standard deviation.

FIG. 10 shows the comparison of different blocker/diluents on the binding of antibodies to SQE. Costar U bottom plates were used. Plates were coated with 100 nmol of SQE. Clone SQE #16 (A) and SQE #18 (B) were diluted 1:10 in PBS, pH 7.4 containing the blocker/diluents indicated. Normal mouse serum (C) and anti-SQE serum (D) were diluted 1:50. The ELISA was performed as described for the standard protocol. Values are the mean of triplicate determination±standard deviation.

FIG. 11 shows the comparison of different amounts of BSA used as the blocker/diluent. Costar U bottom plates were used. Plates were coated with 100 nmol of SQE. Antibodies were diluted in PBS containing the percent BSA indicated. Clone SQE #16 (A) and SQE #18 (B) were diluted 1:10. Normal mouse serum (C) and anti-SQE serum (D) were diluted 1:50. The ELISA was performed as described for the standard protocol. Values are the mean of triplicate determination±standard deviation.

FIG. 12 shows the binding of anti-SQE antibodies to SQE-coated plates as a function of incubation temperature. Plates were coated with 100 nmol of SQE. PBS-2% BSA was used as a blocker/diluent, which was equilibrated to temperature indicated. Clone SQE #16 (A) and the anti-SQE serum (C) were diluted 1:50 and 1:100 respectively. The ELISA was performed as described for the standard assay except the incubations were at the temperature indicated. Values are the mean of triplicate determination±standard deviation.

Figure 13:
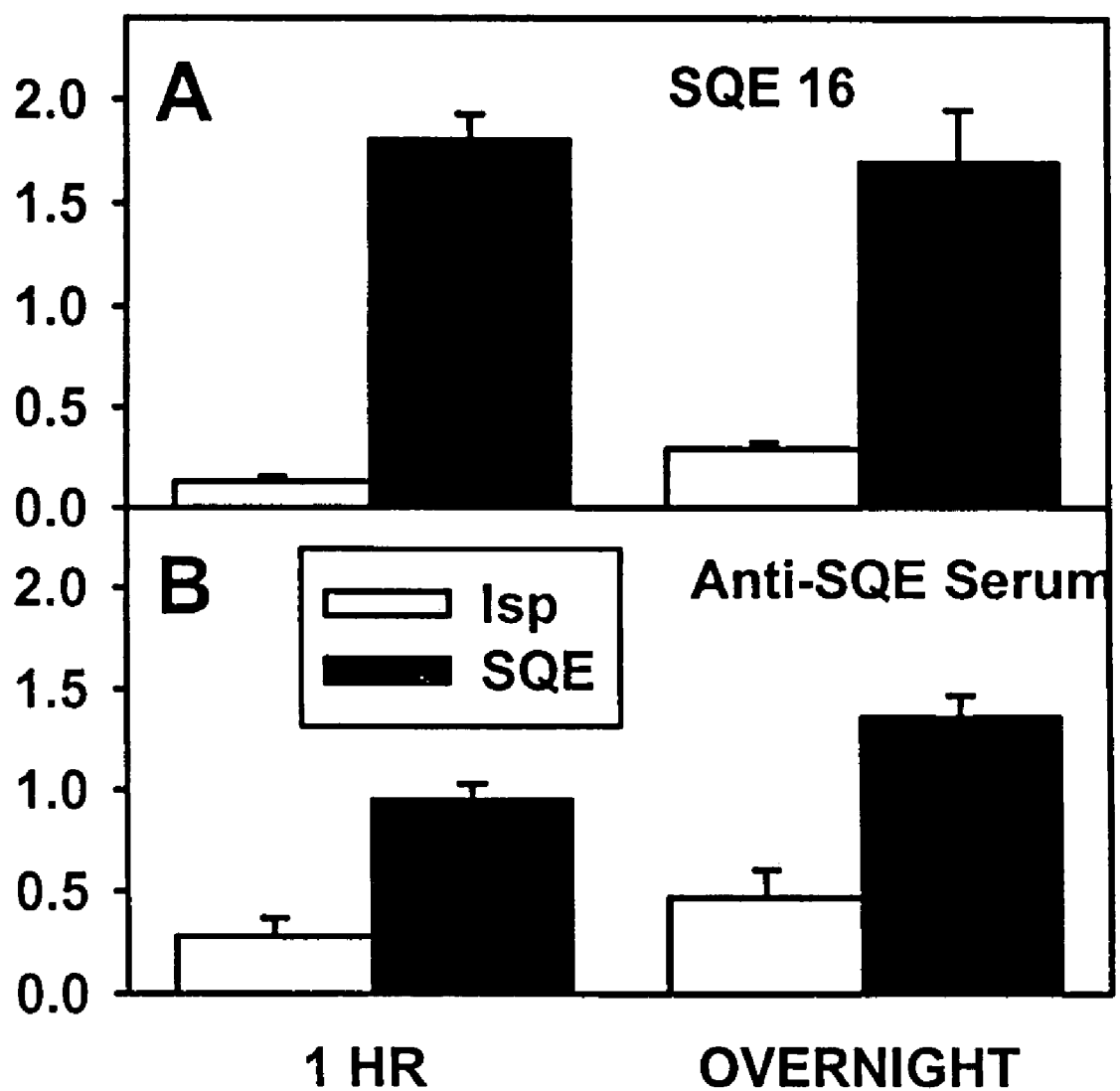

FIG. 13 shows the binding of anti-SQE antibodies to SQE-coated plates as a function of primary antibody incubation time. Plates were coated with 100 nmol of SQE. PBS-2% BSA was used as a blocker/diluent. Clone SQE #16 and the anti-SQE serum were diluted 1:100. The ELISA was performed as described for the standard protocol except for the primary antibody incubation time. Values are the mean of triplicate determination±standard deviation.

Figure 14:
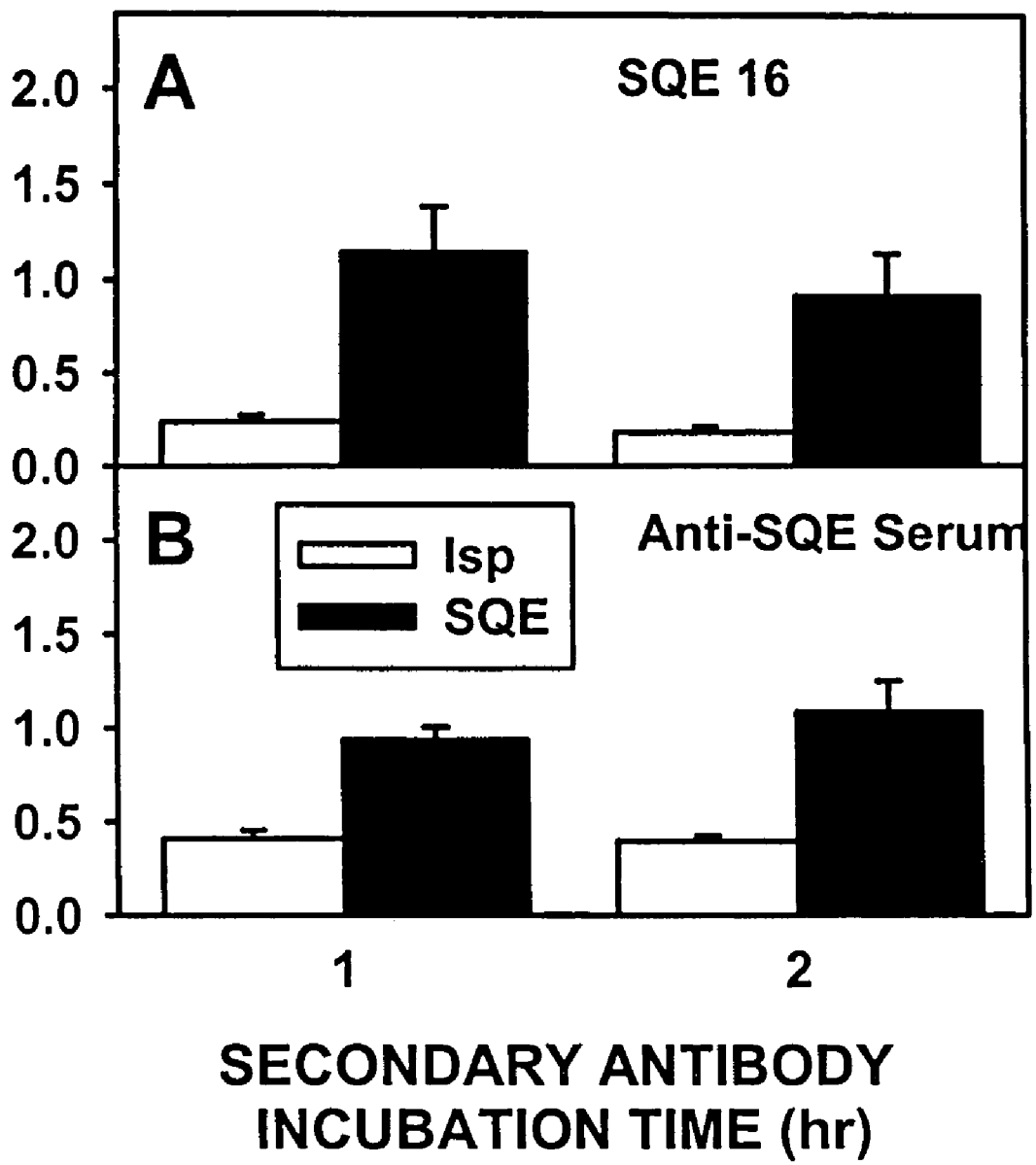

FIG. 14 shows the effect of secondary antibody incubation time on ELISA absorbance of antibodies binding to SQE. Plates were coated with 100 nmol of SQE. PBS-2% BSA was used as a blocker/diluent. Clone SQE #16 and the anti-SQE serum were diluted 1:40 and 1:50, respectively. The ELISA was performed as described for the standard protocol except for the secondary antibody incubation time. Values are the mean of triplicate determination±standard deviation.

Figure 15:
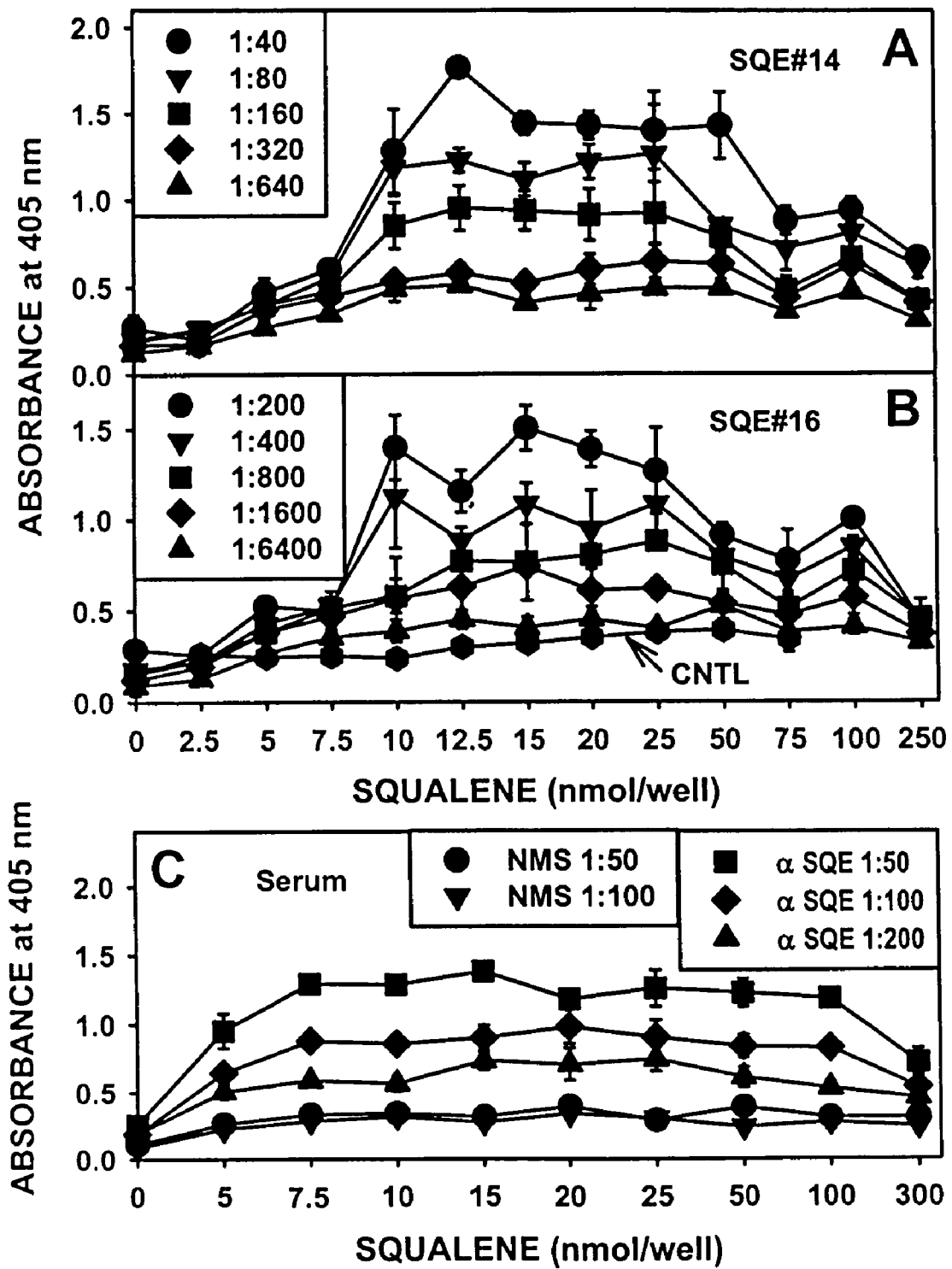

FIG. 15 shows the binding of anti-SQE antibodies as a function of SQE-coated on the well. Plates were coated with the amount of SQE indicated. PBS-2% BSA was used as a blocker/diluent. Clones SQE #14 (A) and SQE #16 (B) and serum (C) was diluted as indicated. The ELISA was performed as described for the standard protocol. Values are the mean of triplicate determination±standard deviation.

Figure 16:
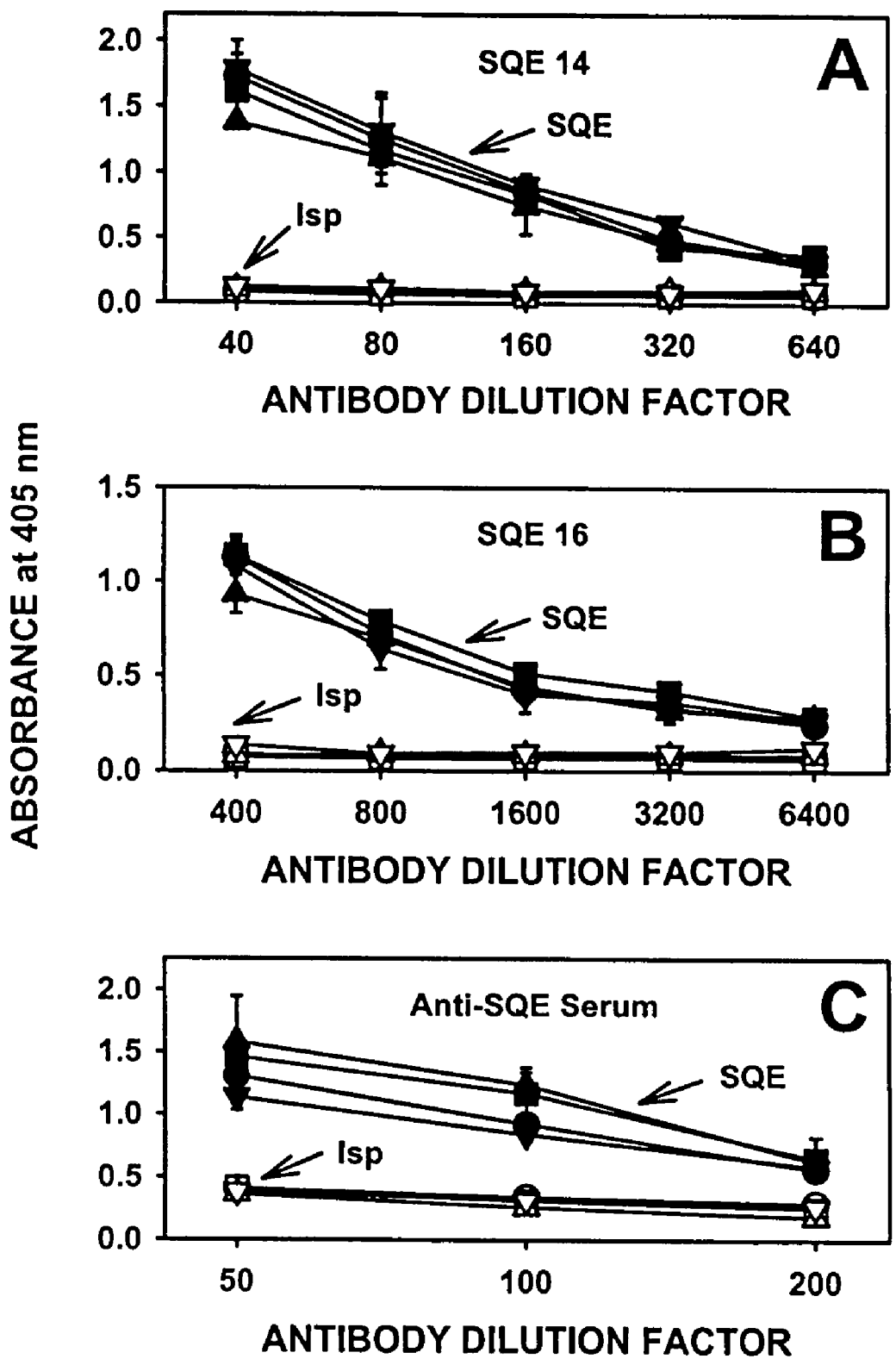

FIG. 16 shows the comparison of different lots of plates. Plates were coated with 10 nmol of SQE. PBS-2% BSA was used as a blocker/diluent. Clone SQE #14 (A), clone SQE #16 (B) anti-SQE serum (C) were used as primary antibodies. The ELISA was performed as described for the standard protocol. Each symbol is a plate with a different lot number. Values are the mean of triplicate determination±standard deviation.

Figure 17:
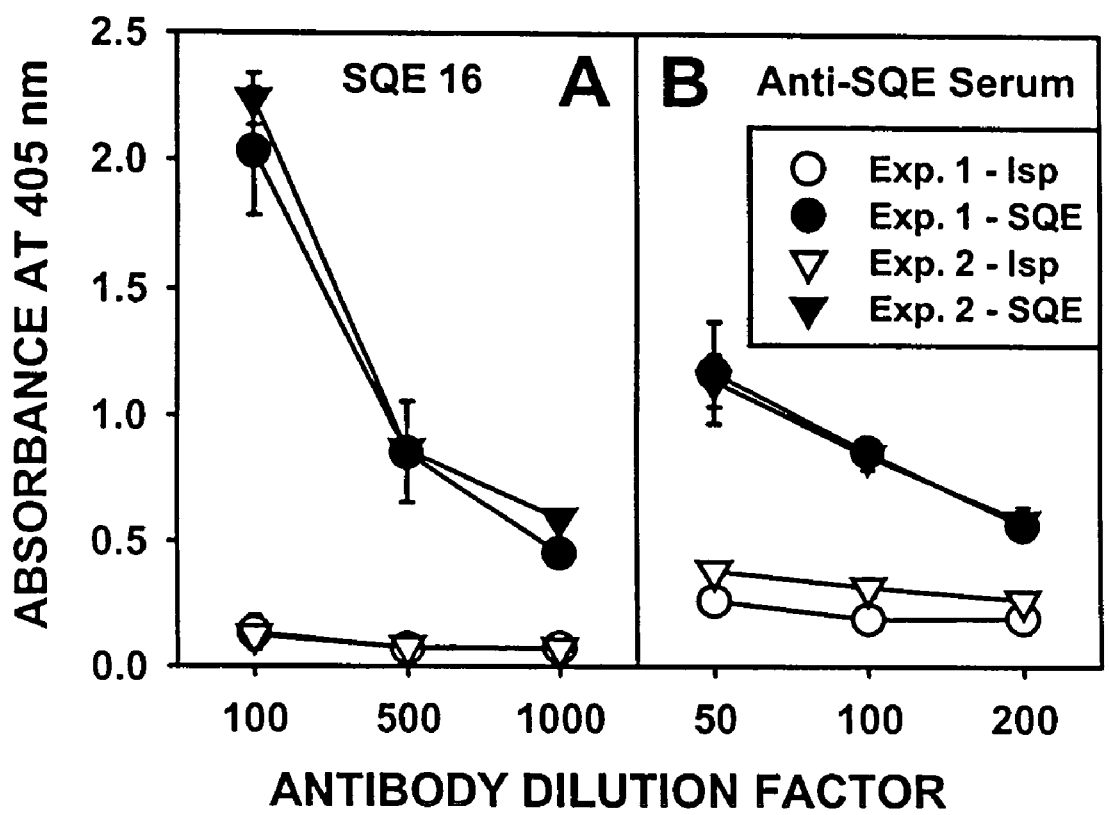
Figure 18:
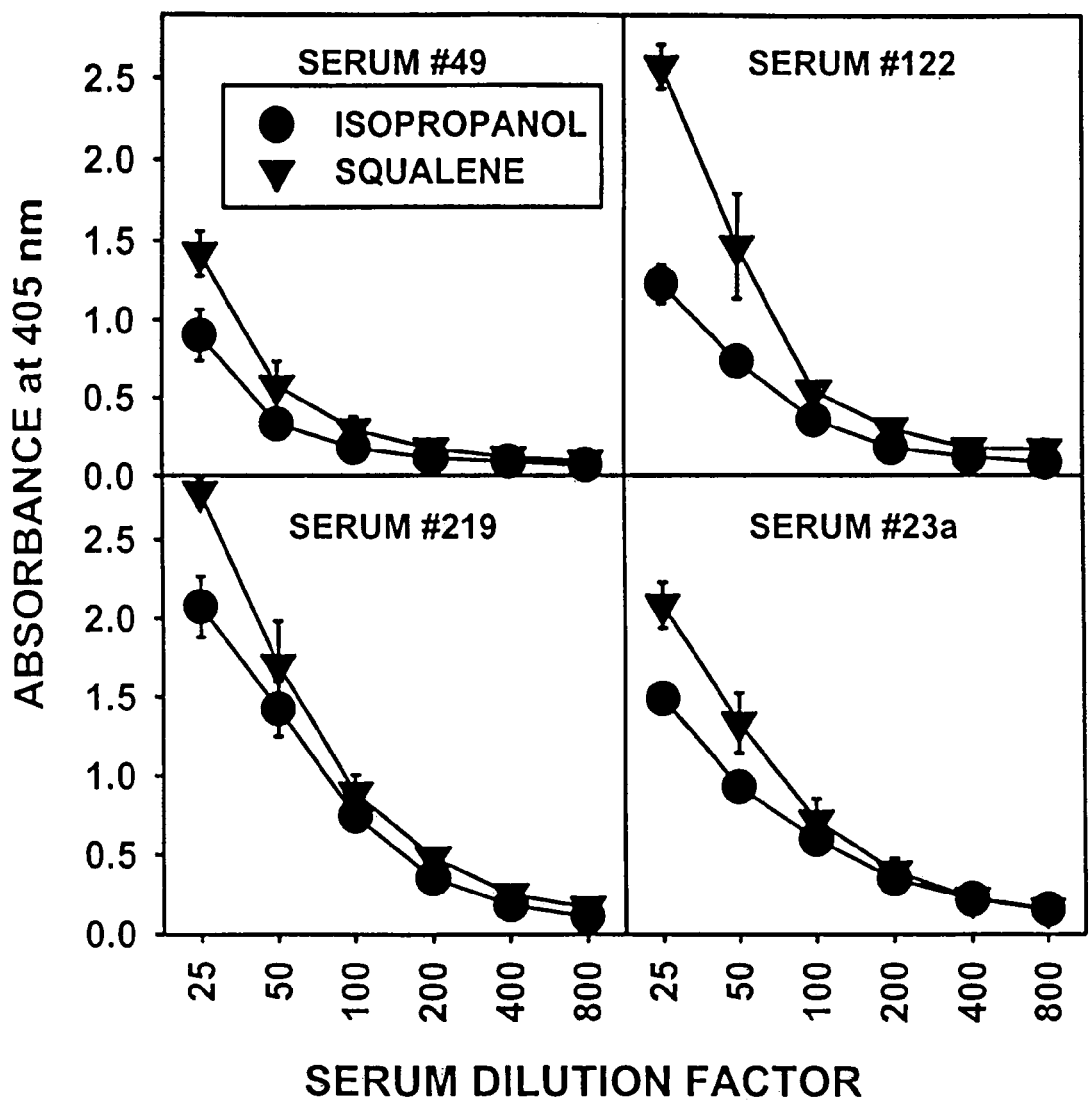
Figure 19:
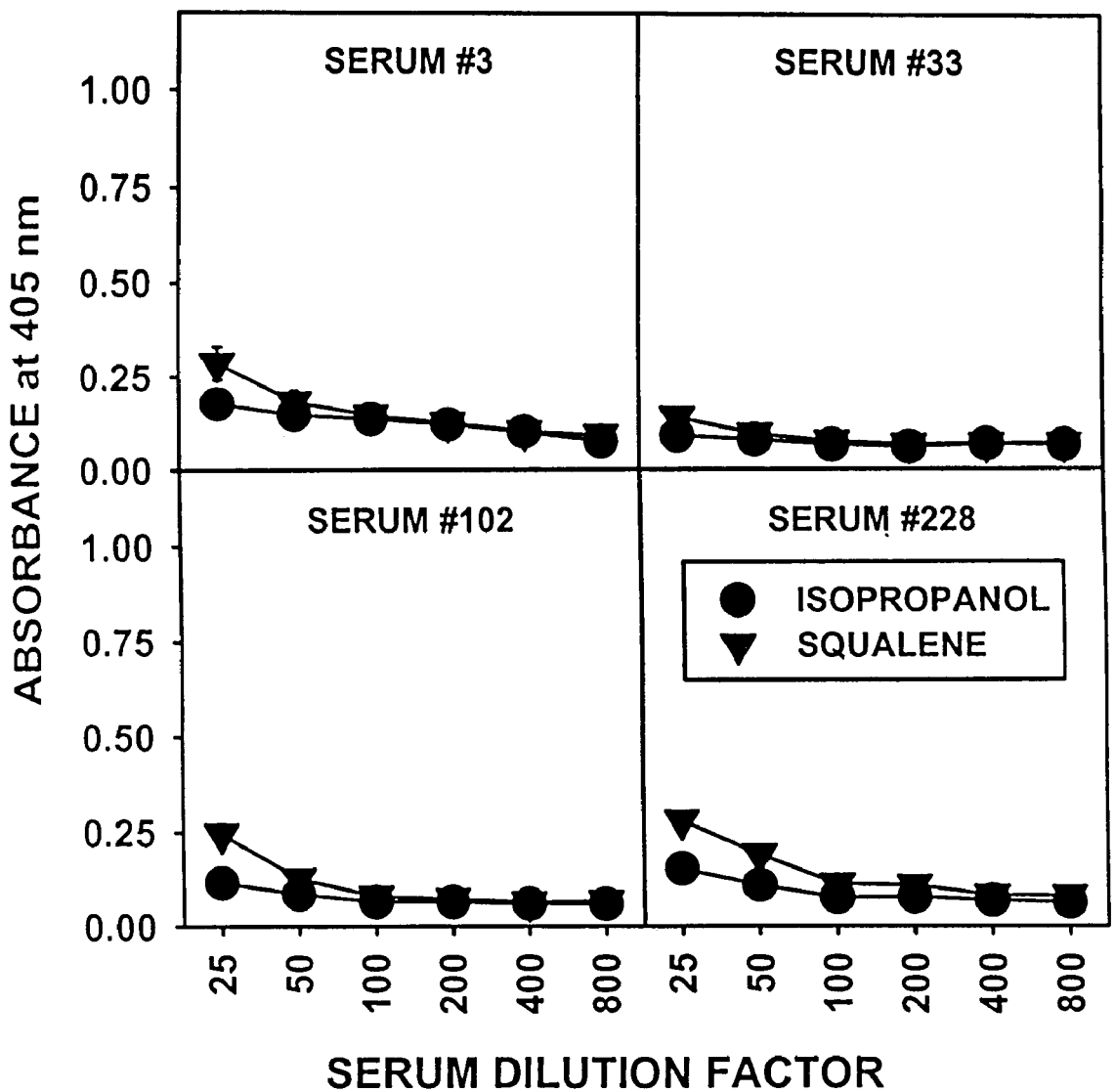
Figure 20:
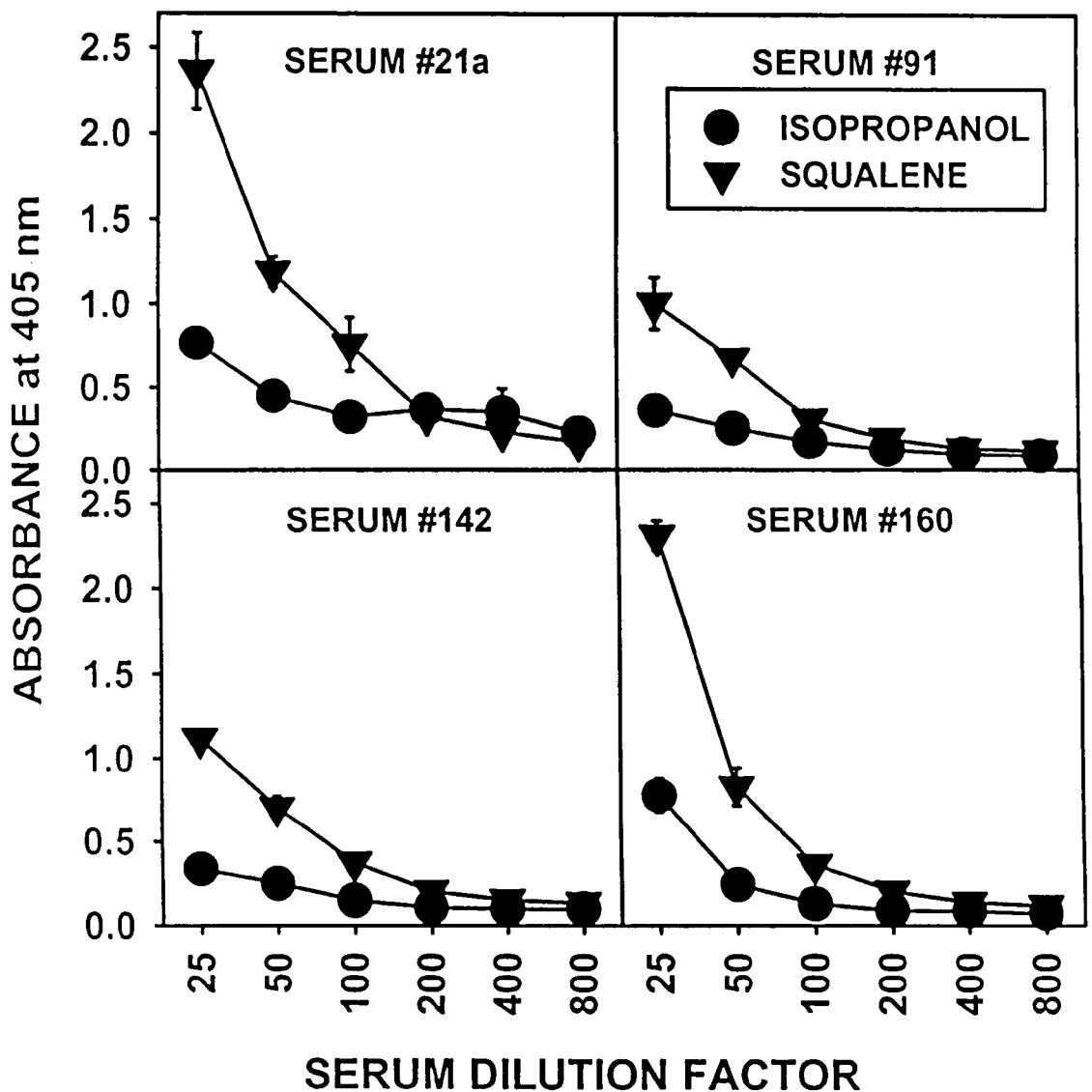
Figure 21:
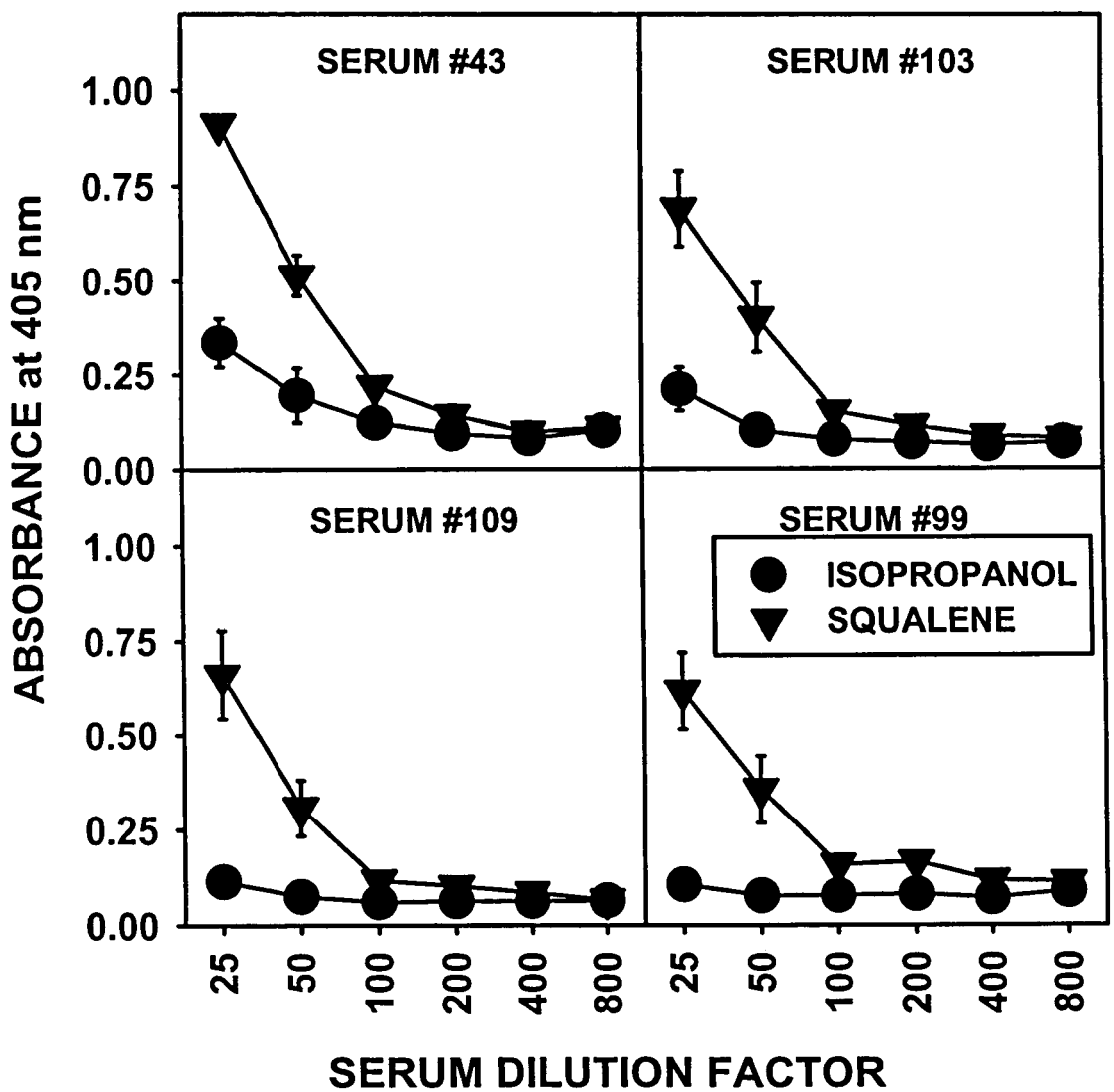
Figure 22:
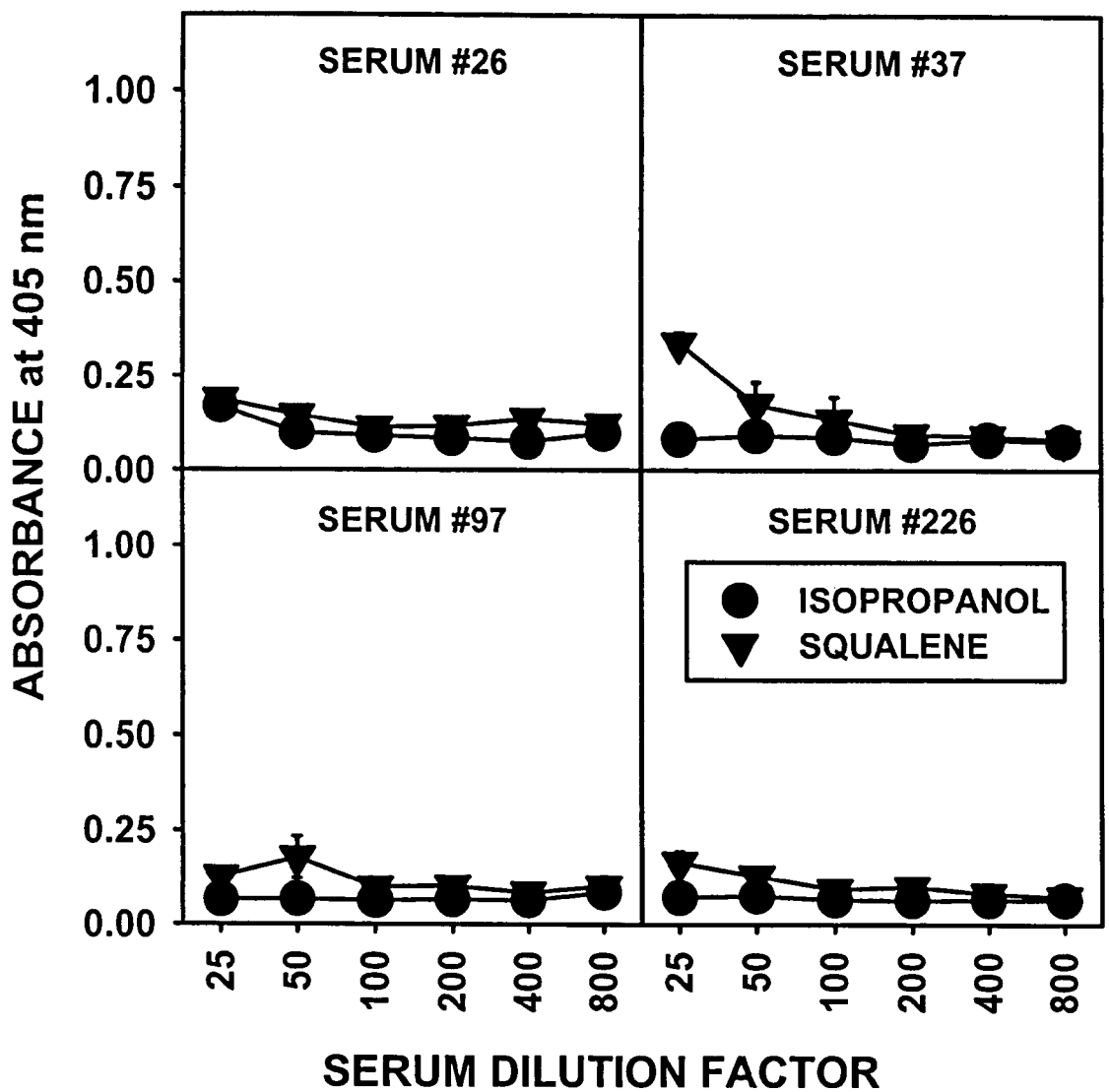

FIG. 17 shows the day to day reproducibility of the ELISA assay for antibodies to SQE. Plates were coated with 10 nmol of SQE. PBS-2% BSA was used as a blocker/diluent. Experiments 1 and 2 were done on separate days using the standard protocol. Values are the mean of triplicate determination±standard deviation.

FIGS. 18-22 shows the results of the experiments described in Example 19, illustrating the applicability of the method of the present invention to detecting anti-squalene antibodies in human sera.

VI. DETAILED DESCRIPTION OF THE INVENTION

The present invention is monoclonal antibody that specifically binds to squalene, and methods for producing the monoclonal antibody. A monoclonal antibody that specifically binds to squalene has been deposited in the American Type Culture Collection, and has received Accession No. PTA 6538 and PTA 6539. "Squalene" refers to a hydrocarbon of the chemical formula $C_{30}H_{50}$ [2,6,10,15,19,23-hexamethyl-2,6,10,14,18,22-tetracosahexaene], CAS Number [111-02-4].

The present invention is also the use of that monoclonal antibody, or a segment or portion thereof, in an immunoassay for the detection of anti-squalene antibodies. "Anti-squalene antibody" refers to an antibody capable of complexing with squalene. Such an antibody may complex with squalene, or with any antigenic epitope presented by squalene.

The present invention is also directed to an immunoassay for detecting anti-squalene antibodies. In preferred embodiments of the invention, the immunoassay is specific for anti-squalene antibodies. In most preferred embodiments of the invention, the immunoassay is capable of differentiating between anti-squalene antibodies and anti-squalane antibodies.

The test sample may generally be any type of biological material containing antibodies. Such materials may be processed so that they are provided in a suitable form. The test sample is preferably provided from a bodily fluid, more preferably is provided from blood, and most preferably provided from serum. The organism providing the test sample may generally be any organism which contains antibodies. The organism preferably is a mammal, and more preferably is a human.

In accordance with some embodiments of the present invention, the immunoassay uses a polystyrene support in combination with certain blockers/diluents. In accordance with the present invention, fetal bovine serum should not be used as a blocker/diluent because it appears to compete with antibody binding in the assay. Not intending to be limited to a particular theory, it is believed that fetal bovine serum itself includes an amount of squalene sufficient to block or diminish antibody binding.

In preferred embodiments of the invention, the assay uses a blocker/diluent that does not compete with squalene and/or anti-squalene antibodies. Exemplary blockers/diluents suitable for use with polystyrene supports include but are not limited to phosphate buffered saline (PBS), bovine serum albumin (BSA), gelatin, casein, or combinations or mixtures thereof. Preferred blockers/diluents include BSA; most preferred blockers/diluents include BSA and PBS. As noted in more detail in the Examples, the preferred amount of BSA is up to about 5% by volume BSA, for example, from about 1% to about 2%.

In accordance with some embodiments of the present invention, the immunoassay may use a hydrophobic membrane support, preferably polyvinylidene difluoride.

In accordance with the present invention, any assay suitable for use with a monoclonal antibody or antibody fragment may be used to detect squalene antibodies. Preferred assays are a radioimmunoassay and ELISA.

The present invention also includes preparing a monoclonal antibody that specifically binds to or reacts with squalene. In preferred embodiments of the invention, the monoclonal antibody binds to squalene but not squalane (hydrogenated form of squalene).

The present invention also includes a method for detecting anti-squalene antibodies. The present invention also includes a method for selectively detecting anti-squalene antibodies, i.e., differentiating between anti-squalene antibodies and anti-squalane antibodies.

The present invention also includes a kit for detecting anti-squalene antibodies, said kit including one or more of the following: components used for a radioimmunoassay; components used for ELISA; one or more monoclonal antibodies; one or more antibody fragments; one or more washes; one or more buffers; one or more detection agents or labels, including but not limited to peroxidase; and one or more solid supports configured and suitable for use with the particular assay being conducted. A diagnostic kit may be designed to aid the performance of the above method. Such a kit may contain vessels containing squalene and the indicator regent, respectively.

Exemplary solid supports include but are not limited to polystyrene or polyvinyldiene fluoride (PVDF).

Each of these elements will now be described in more detail.

Exemplary binding agents include, but are not limited to: monoclonal antibodies ("MAb"); chimeric monoclonal antibodies ("C-MAb"); humanized antibodies; genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); antigen-binding peptides; tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; any of the above joined to a molecule that mediates an effector function; and mimics or fragments of any of the above. The binding agent may be labeled or unlabeled.

A binding agent according to the invention is preferably a monoclonal or polyclonal antibody. The antibody includes, but is not limited to native or naked antibodies; modified antibodies, such as activated or photoactivated antibodies. As used herein, native refers to a natural or normal antibody; naked refers to removing a non-native moiety, e.g., removing the label from a labeled antibody.

Methods for producing and obtaining an antibody are well known by those skilled in the art. An exemplary method includes immunizing any animal capable of mounting a usable immune response to the antigen, such as a mouse, rat, goat sheep, rabbit or other suitable experimental animal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced. Fragments of binding agents, may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light will enhance the immune response to a multi-epitopic antigen under similar conditions. Various binding agents, antibodies, antigens, and methods for preparing, isolating, and using the binding agents are described in U.S. Pat. No. 4,471,057 (Koprowski), U.S. Pat. No. 5,075,218 (Jette, et al.), U.S. Pat. No. 5,506,343 (Fufe), and U.S. Pat. No. 5,683,674 (Taylor-Papadimitriou, et al), all incorporated herein by reference. Furthermore, many of these antibodies are commercially available from Centocor, Abbott Laboratories, Commissariat a L'Energie Atomique, Hoffman-LaRoche, Inc., Sorin Biomedica, and FujiRebio.

The compositions and methods of the present invention are suitable for use in any immunoassay capable of detecting an antibody or the like bound to an antigen. Exemplary assays include labeled binding reagent assays, including noncompetitive and competitive binding assays, including assays in which the solid phase is the binding reagent or the ligand, and sandwich assays, including precipitation, radioimmunoassay, or enzyme-linked immunosorbent assay. It is intended that the invention is not to be limited by the type of immunoassay employed or the specific protocol used in performing the assay. Exemplary immunoassays techniques are shown in the Examples.

The squalene provided in the above method may be immobilized on a solid support. The solid support may be provided in one of many different forms. These forms may include a membrane, filter, plastic, bead, agarose bead, SEPHAROSE (SEPHAROSE is a registered trademark of Pharmacia Biotech, Piscataway, N.J.) Bead, or magnetic bead.

In addition to the different forms, the solid support may be made from a variety of materials. The solid support is preferably nitrocellulose, polyvinylidene difluoride, nylon, rayon, cellulose acetate, agarose, SEPHAROSE, metal, polypropylene, polyethylene, polystyrene, polyvinyl chloride, polyvinyl acetate, polyamide, polyimide, polycarbonate, polyether, polyester, polysulfono, polyacetal, or polymethyl methacrylate, more preferably is polypropylene, polystyrene, polyvinylchloride, polyamide, polycarbonate, polyether, polymethyl methacrylate, nitrocellulose, polyvinylidene difluoride, or nylon, and most preferably is nitrocellulose.

The squalene may generally be from any source. Commercial preparations are readily available (Sigma, St. Louis, Mo.). Alternatively, it may be synthesized from various precursors or obtained from an organism. Squalene is a relatively large hydrocarbon which may contain multiple antigenic epitopes. As a result any portion of squalene containing and antigenic epitope may be used in place of squalene in the present invention.

It is preferred that during the assay process, substantially all of at least one predetermined ligand or ligand receptor remains in a predetermined position. Any technique for immobilizing a ligand or ligand receptor is included in the scope of the present invention. In a preferred embodiment, a ligand or ligand receptor is bound or immobilized on or in a solid phase. Typical immobilization mechanisms include, but are not limited to, covalent binding, non-covalent binding, chemical coupling, physical entrapment, and adsorption.

Included within the scope of the present invention is changing or incorporating different surface properties on the membrane in order to achieve a desired result, e.g., the surface properties of a membrane designed for a competitive binding assay for a hormone may be different than an immunometric assay for a therapeutic drug. For example, it has been shown that treating the surface of a hydrophilized PVDF membrane with ethanolamine reduces the non-specific binding of the membrane surface. Selection of a particular surface treatment agent or surface property may be based on the desired chemical characteristic to be imparted to the surface; the inability or reduced capability of denaturing or impairing the functionality of a bioactive agent on or in the reaction zone; the desire to effect a certain orientation of an immobilized bioactive molecule; the desire to promote long-term stability of an immobilized bioactive molecule; the inclusion of a desired nucleophilic substituent; and the availability and cost of treatment agents. The use of other surface treatment agents, including bi-functional or multi-functional reagents, to affect the surface properties of the membrane are included within the present invention.

There are many other suitable detection methods compatible with the instant invention. In each case, the detection agent and its method of use are well known to one of ordinary skill in the art. The indicator reagent is typically conjugated to a detectable label. The detectable label may be an enzyme, such as alkaline phosphatase, β-galactosidase, or peroxidase; a protein, such as biotin or digoxin; a fluorochrome, such as rhodamine, phycoerythrin, or fluourescein; a fluorescent protein, such as GFP or one of its many modified forms; a radioisotope; or a nucleic acid segment. Enzymes, such as horseradish peroxidase, alkaline phosphatase, and β-galactosidase, may also be used as detectable labels. Detection agents for enzymes generally utilize a form of the enzyme's substrate. The substrate is typically modified, or provided under a set of conditions, such that a chemiluminescent, colorimetric, or fluorescent signal is observed after the enzyme and substrate have been contacted (Vargas, et al. Anal Biochem 209: 323, 1993).

A signal-producing agent refers to any agent or marker which produces a detectable signal or which permits the detection of a ligand or ligand-receptor. Preferred signal-producing agents are those which permit detection of the analyte without instruments, preferably by visual means. Exemplary signal-producing agents include, but are not limited to color forming agents, such as an enzyme, polymer containing dyes, chemiluminescent agents, fluorescent agents, radioisotopes or ferromagnetic particles. The color forming agent may be a colored particle, a colored molecule or some species, such as an enzyme, which is capable of triggering a sequence of events leading to the formation of a colored marker. The colored molecule may be a fluorescent dye, such as fluorescein or rhodamine; a chemiluminescent compound; a bioluminescent compound; or a compound that may be detected by the absorption of electromagnetic radiation (and possible reemission of radiation at another wavelength), including ultraviolet radiation, visible radiation and infrared radiation. The colored molecule may be directly or indirectly conjugated to a ligand or ligand-receptor. Alternatively, the colored molecule may be incorporated in a particle, particularly a microsome.

Enzymes, useful as color forming agents, include alkaline phosphatase, horseradish peroxidase or B-galactosidase. Such enzymes are often used in conjunction with a chromogenic substrate.

I the methods of the present invention, it may be desirable to control or specify the amount of squalene bound to the solid support. Determining the appropriate amount of squalene for a particular assay is well within the capability of one skilled in the art. The present inventors have found that, for the murine assays shown in the Examples, up to about 100 nmol, preferably between about 7.5 and about 100 nmol, and most preferably, between about 10 and about 25 nmol of squalene yields a reproducible assay. For the human assays shown in the Examples, up to about 500 nmol, preferably between about 7.5 and about 100 nmol, and most preferably, between about 7.5 and about 20 nmol of squalene yields a reproducible assay.

REFERENCES

Alving, C. R. 1986. Antibodies to liposomes, phospholipids, and phosphate esters. Chem. Phys. Lipids 40, 303.

Alving, C. R., Grabenstein, J. 2000. Letter to the editor. Exp. Mol. Path. (in press).

Alving, C. R., Swartz, Jr., G. M. 1991. Antibodies to cholesterol, cholesterol conjugates, and liposomes: Implications for atherosclerosis and autoimmunity. Crit. Rev. Immunol. 10, 441.

Alving, C. R. and Wassef, N. M. 1999. Naturally-occurring antibodies to cholesterol: a new theory of LDL cholesterol metabolism. Immunology Today 20, 362.

Alving, C. R., Shichijo, S., Mattsby-Baltzer, I., Richards, R. L., Wassef, N. M. 1993. Preparation and use of liposomes in immunological studies. In: G. Gregoriadis (Ed.) Liposome Technology, vol. 3, (Second Edition), CRC Press, Inc., Boca Raton, p. 317.

Alving, C. R., Swartz, Jr., G. M., Wassef, N. M. 1989. Naturally-occurring autoantibodies to cholesterol in humans. Biochem. Soc. Trans. 17 637.

Alving, C. R., Swartz, Jr. G. M., Wassef, N. M., Ribas, J. L., Herderick, E. E., Virmani, R., Kolodgie, F. D., Matyas, G. R., Cornhill, J. F. 1996. Immunization with cholesterol-rich liposomes induces anti-cholesterol antibodies and reduces diet-induced hypercholesterolemia and plaque formation. J. Lab. Clin. Med. 127, 40.

Alving, C. R., Wassef, N. M., Potter, M. 1996. Antibodies to cholesterol: biological implications of antibodies to lipids. Curr. Topics Microbiol. Immunol. 210, 181.

Asa, P., Cao, Y., Garry, R. F. Antibodies to squalene in gulf war syndrome. 2000. Exp. Mol. Path. 68, 55.

Aniagolu, J., Swartz, Jr., G. M., Dijkstra, J., Madsen, J. W., Raney, J. J., Green, S. J. 1995. Analysis of anticholesterol antibodies using hydrophobic membranes. J. Immunol. Meth. 182, 85.

Banerji, B., Alving, C. R. 1981. Anti-liposome antibodies induced by lipid A. I. Influences of ceramide, glycosphingolipids, and phosphocholine on complement damage. J. Immunol. 126, 1080.

Dijkstra, J., Swartz, Jr., G. M, Raney, J. J., Aniagolu, J., Toro, L., Nacy, C. A., Green, S. J. 1996. Interaction of anti-cholesterol antibodies with human lipoproteins. J. Immunol. 157, 2006.

Granner, D. K. 1996. Hormones of the adrenal cortex. In: R. K. Murray, D. K. Granner, P. A. Mayes and V. W. Rodwell (Eds.) Harper's Biochemistry, $24^{th}$ Edition, Appleton & Lang, Stamsord, p. 547.

Galfré, G., Milstein, C. 1981. Monoclonal antibodies: strategies and procedures. Meth. Enzymol. 73, 3.

Gupta, R. K., Varanelli, C. L., Griffin, P., Wallach, D. F. H., Siber, G. R. 1996. Adjuvant properties of non-phospholipid liposomes (Novasomes®) in experimental animals for human vaccine antigens. Vaccine 14, 219.

Köhler, G., Milstein, C., 1975. Continuous cultures of fused cells secreting antibody of predefined specificity. Nature 256, 495.

Lohner, K., Degovics, G., Laggner, P., Gnamusch, E., Paltauf, F. 1993. Squalene promotes the formation of non-bilayer structures in phospholipid model membranes. Biochim. Biophys. Acta 1152, 69.

Koivisto, P. V. I., Miettinen, T. A. 1988. Increased amount of cholesterol precursors in lipoproteins after ileal exclusion. Lipids 23, 993.

Mayes, P. A. 1996. Cholesterol synthesis, transport, & excretion. In: R. K. Murray, D. K. Granner, P. A. Mayes and V. W. Rodwell (Eds.) Harper's Biochemistry, $24^{th}$ Edition, Appleton & Lang, Stamsord, p. 271.

Miettinen, T. A. 1982. Diurnal variation of cholesterol precursors squalene and methyl sterols in human plasma lipoproteins. J. Lipid Res. 23, 466.

Minutello, M., Senatore, F., Cecchinelli, g., bianchi, M., Andreani, t., Podda, A., Crovari, P. 1999. Safety and immunogenicity of an inactivated subunit influenza virus vaccine combined with MF59 adjuvant emulsion in elderly subjects, immunized for three consecutive influenza seasons. Vaccine 17, 99.

Schuster, B., Neidig, M., Alving, B. M., Alving, C. R. 1979. Production of antibodies against phosphocholine, phosphatidylcholine, sphingomyelin, and lipid A by injection of liposomes containing lipid A. J. Immunol. 122, 900.

Stewart, M. E. 1992. Sebaceous gland lipids. Semin. Dermatol. 11, 100.

Swartz, Jr., G. M., Gentry, M. K., Amende, L. M., Blanchette-Mackie, E. J., Alving, C. R. 1988. Antibodies to cholesterol. Proc. Natl. Acad. Sci. U.S.A. 85, 1902.

Stollar, B. D., McInerney, T., Gavron, T., Wassef, N. M., Swartz, G. M., Jr., Alving, C. R. 1989. Cross-reactions of nucleic acids with monoclonal antibodies to phosphatidylinositol phosphate and cholesterol. Mol. Immunol. 26, 73.

Wassef, N. M., Roerdink, F., Swartz, Jr., G. M., Lyon, J. A., Berson, B. J., Alving, C. R. 1984. Phosphate binding specificities of monoclonal antibodies against phosphoinositides in liposomes. Mol. Immunol. 21 863.

EXAMPLES

Materials and Methods

Lipids

Squalene, squalane oils, and bovine serum albumin (essentially fatty acid free; cat. # A-7030) (BSA) were purchased from Sigma-Aldrich Chemical Company, St. Louis, Mo. Isopropanol was purchased from J. T. Baker, Phillipsburg, N.J. Emulsifiers for creating oil-in-water emulsions consisted of Span 85 and Arlacel A (both from Sigma) and Tween 80 (Aldrich Chemical Co., Milwaukee, Wis.). Dimyristoyl phosphatidylcholine (DMPC) and dimyristoyl phosphatidylglycerol (DMPG), both used in the formation of liposomes, were purchased from Avanti Polar Lipids, Alabaster, Ala. Lipid A from *Salmonella minnesota* R595 was purchased from List Biological Laboratories, Campbell, Calif. PVDF plates (Multiscreen-IP) were from Millipore, Bedford, Mass. Immullon 2 U and flat bottom and Immulon 4HBX 96 well ELISA plates were from Dynex, Chantily, Va. F96 Maxisorp 96 well ELISA plates were from Nalge Nunc International Corp., Naperville, Ill. Flat and U bottom tissue culture plates were from Costar-Corning, Corning, N.Y. FBS was from GIBCO BRL, Grand Island N.Y. and was heated at 56° C. for 1 h prior to use. Gelatin was from BioRad Laboratories, Richmond, Calif. Seal plate adhesive film was from PGC Scientific, Gaithersburg, Md. Affinity purified and adsorbed peroxidase-linked sheep anti-mouse IgM was from The Binding Site, San Diego, Calif. ABTS substrate was purchased from Kikegaard and Perry Laboratories, Gaithersburg, Md. Female Balb/c mice were purchased from Jackson Laboratories, Bar Harbor, Me.

Immunologic and Culture Reagents

Aluminum hydroxide gel, Alhydrogel, was purchased from Superfos Biosector, Vedbaek, Denmark. Mouse myeloma X63/Ag8.653 was purchased from American Type Culture Collection, Chantilly, Va. Polyethylene glycol 1500 was from Boehringer Mannheim, GmbH, Germany. Dulbecco's modified Eagle's medium with high glucose (DMEM), MEM sodium pyruvate (100 mM), MEM nonessential amino acids (NEAA) (100×), penicillin (10,000 units/ml)-streptomycin (10,000 µg/ml), 200 mM glutamine, 100×HAT (10 mM sodium hypoxanthine, 40 µM aminopterin, 1.6 mM thymidine) 100×HT (10 mM sodium hypoxanthine and 1.6 mM thymidine) supplements, Hank's Balanced Salts Solution, and fetal bovine serum were from GIBCO BRL, Grand Island, N.Y. Fetal bovine serum was heated at 56° C. for 1 hour prior to use. Peroxidase-linked goat anti-mouse IgM and peroxidase-linked goat anti-mouse IgG were purchased from The Binding Site, San Diego, Calif. ATBS substrate was purchased from Kirkegaard & Perry Laboratories, Gaithersburg, Md. Gelatin was from BioRad Laboratories, Richmond, Calif. Polystyrene Immulon II ELISA plates "U" and flat bottom were from Dynex, Chantilly, Va. PVDF Multiscreen-IP plates were from Millipore Corp., Bedford Mass. and adapted for ELISA. Seal plate adhesive film was from PGC Scientific, Gaithersburg, Md. Sterile Dulbecco's phosphate buffered saline lacking calcium and magnesium (PBS) was from BioWhittaker, Walkersville, Md. Nonsterile PBS was prepared from standard laboratory salts.

Manufacture of Liposomes

Liposomes containing SQE or SQA were prepared by a modification of the method of Alving et al. (1993). DMPC and DMPG were dissolved in chloroform at 180 mM and 20 mM, respectively. Lipid A was dissolved in chloroform at a concentration of 1 mg/ml. Glassware was depyrogenated overnight at 250° C. Chloroform solutions of lipids, including SQE or SQA, as appropriate, were placed in a pear shaped flask, and the chloroform was removed by rotary evaporation. The neck of the flask was covered with sterile Whatman 541 filter paper to maintain sterility. The dried lipid film was placed under high vacuum (50 mbar) for at least 1 hr. PBS was added to the dried lipid film to give a final phospholipid concentration of 100 mM. After closing with a ground glass stopper, the flask was shaken until all of the dried lipids were in suspension. Liposomes were stored at 4° C.

Liposomes Containing 43% Squalene for Immunization (Group 3)

Liposomes containing low amounts of SQE (43 mol %) were made with DMPC:DMPG:SQE in a molar ratio (9:1:7.5). Lipid A was added to give a final dose of 25 µg in 0.2 ml of 100 mM phospholipid. Six ml of DMPC, 6 ml of DMPG, 1.5 ml of lipid A, and 0.438 ml of SQE were added to a 100 ml pear shaped flask. After drying as described above, PBS was added to give a final volume of 12 ml.

Liposomes Containing 71% Squalene for Immunization (Group 4)

Liposomes containing high amounts of SQE (71 mol %) were made with DMPC:DMPG:SQE in a molar ratio (9:1:25). Lipid A was added to give a final dose of 25 µg in 0.2 ml of 100 mM liposomal phospholipid. Six ml of DMPC, 6 ml of DMPG, 1.5 ml of lipid A, and 1.46 ml of SQE were added to a 100 ml pear shaped flask. After drying as described above, PBS was added to give a final volume of 12 ml.

Liposomes Used for ELISA

Liposomes used for ELISA were made with DMPC:DMPG or DMPC:DMPG:SQE (or SQA, as appropriate), in molar ratios of 9:1 or 9:1:7.5. Twenty ml of DMPC, 20 ml of DMPG, and 1.44 ml of SQE or 1.6 ml of SQA (or no oil antigen) were added to a 100 ml pear shaped flask. After drying as above, PBS was added and the final volume of the liposomes was adjusted to 20 ml. The liposomes are designated L(SQE) for SQE-containing liposomes, L(SQA) for SQA-containing liposomes, or L for liposomes lacking an oil antigen. The final phospholipid concentration was 100 mM.

Preparation of Emulsions for Immunization

Emulsion with 40% SQE, 10% Arlacel A, and Lipid A (Group 5)

Components for this formulation were initially prepared in two separate 2 ml vaccine vials. One vial contained 1 ml of saline. For the second vial, 2.5 mg of lyophilized lipid A was dissolved in 8 ml of SQE; 2 ml of Arlacel A were then added; and 1 ml of the combination was added to the vial. The emulsion was prepared just prior to injection by emulsifying 0.75 ml of saline with 0.75 ml SQE-Arlacel A-lipid A using 2 three ml plastic syringes and a 3-way stopcock. The saline was drawn into one syringe and the SQE-Arlacel A-lipid A was drawn into another syringe. The saline was pushed into the SQE-Arlacel A-lipid A. The mixture was passed back and forth at a rate of approximately 2 passes/sec for 5 min. to form an emulsion. The emulsion was stable for several hours at room temperature.

Emulsion with 20% SQE, 5% Tween 80, 5% Span 85, and Lipid A (Group 6)

Components were vialed in two separate 2 ml vaccine vials prior to emulsification. One vial contained 1.5 ml of saline. The components for the second vial were made by dissolving 12 mg of lyophilized lipid A in 14.4 ml of SQE. Tween 80 (7.2 ml) and Span 85 (7.2 ml) were added to the lipid A in SQE. One ml of the mixture was vialed. The emulsion was prepared just prior to injection by emulsifying 1.05 ml saline with 0.45 ml SQE-Tween 80-Span 85-lipid A using 2 three ml plastic syringes and a 3-way stopcock as described above. The emulsion was unstable and separated into 2 layers in approximately 45 min.

Aluminum Hydroxide Gel Mixed with Emulsion Containing 19% Squalene, 1% Tween 80 and Lipid A (Group 7)

Aluminum hydroxide was diluted in saline to give 1.25 mg $Al^{+3}$/ml and 1.5 ml was placed in a 2 ml vaccine vial. The components for the second vial were made by dissolving 4 mg of lyophilized lipid A in 6 ml of SQE. Tween 80 (0.32 ml) was added and 1.5 ml of the mixture was added to a 2 ml vaccine vial. The formulation was prepared just prior to injection by emulsifying 1.2 ml of aluminum hydroxide in saline with 0.3 ml of SQE-Tween 80-lipid A, as described above. The final aluminum hydroxide concentration was 1 mg $Al^{+3}$/ml. The mixture was unstable and separated into 2 layers in less than 30 min.

Aluminum Hydroxide Gel Mixed with Emulsion Containing 40% Squalene, 10% Arlacel A, and Lipid A (Group 8)

Aluminum hydroxide was diluted in saline to give 2 mg $Al^{+3}$/ml, and 1.5 ml was added to a 2 ml vaccine vial. The components for the second vial were the same SQE-lipid A-Arlacel A mixture used in group 5. The formulation was prepared just prior to injection by mixing 0.75 ml of aluminum hydroxide in saline with 0.75 ml of SQE-Arlacel A-lipid A, as described above. The final aluminum hydroxide was 1 mg $Al^{+3}$/ml. The mixture was unstable and separated into 2 layers in less than 30 min.

TABLE I

Summary of Immunization groups

| Group No. | Antigen Composition* |
|---|---|
| 1 | Squalene alone (0.5 ml) |
| 2 | Squalene (0.5 ml) mixed with 25 µg of lipid A |
| 3 | Liposomes containing both lipid A and 43 mol % squalene |
| 4 | Liposomes containing both lipid A and 71 mol % squalene |
| 5 | Emulsion containing 40% squalene, 10% Arlacel A, and lipid A |
| 6 | Emulsion containing 20% squalene, 5% Tween 80, 5% Span 85, and lipid A |
| 7 | Aluminum hydroxide gel mixed with emulsion containing 19% squalene, 1% Tween 80 and lipid A |
| 8 | Aluminum hydroxide gel mixed with emulsion containing 40% squalene, 10% Arlacel A and lipid A |

*All injections were administered i.p. in a 0.2 ml dose, except where indicated. Lipid A, when used, was administered at 25 µg of lipid A/dose.

Example 1

Immunizations

BALB/c mice, purchased from Jackson Labs. (Bar Harbor, Me.), were immunized i.p. and bled every 2 weeks under a protocol approved by the institutional Laboratory Animal Care and Use Committee. They were fed standard mouse chow and water ad libitum. Groups of five mice received one of the following immunogens: Group 1—0.5 ml SQE; Group 2—0.5 ml of SQE containing 25 µg lipid A; Group 3—0.2 ml of 43% SQE liposomes; Group 4—0.2 ml of 71% SQE liposomes; Group 5—0.2 ml of emulsion containing 50% saline (0.9% sodium chloride), 40% SQE, 10% Arlacel A containing 25 µg lipid A/dose; Group 6—0.2 ml of an emulsion containing 70% saline, 20% SQE, 5% Tween 80, 5% Span 85 (v/v) containing 25 µg lipid A/dose; Group 7—0.2 ml aluminum hydroxide in saline, 19% SQE, 1% Tween 80, containing 25 µg lipid A/dose; Group 8—0.2 ml of aluminum hydroxide in saline, 40% SQE, 10% Arlacel A containing 25 µg lipid A/dose (Table I). Animals were boosted every 2 weeks. Three additional mice were immunized by the intravenous route with 0.2 ml of the high SQE liposomes (group 4). Three days later, the animals were euthanized and the spleens removed for production of monoclonal antibodies.

Example 2

Production of Monoclonal Antibodies

Three days after the primary or boosting immunization, mice were euthanized and spleens obtained. Single cell suspensions of spleen cells were prepared. Spleen cells and mouse myeloma X63/Ag8.653 cells were fused in a 1:1 ratio using polyethylene glycol 1500 (Köhler and Milstein, 1975; Galfré and Milstein, 1981). After fusion, the cells were centrifuged and then suspended in DMEM containing 20% fetal bovine serum, 1 mM sodium pyruvate, 1×NEAA, 4 mM glutamine, 50 units/ml penicillin, 50 µg/ml streptomycin, 1×HT (30 ml/spleen). Cells (0.1 ml/well) were plated in 96 well plates. The next day 0.1 ml of DMEM media containing 1×HAT instead of HT was added to all of the wells. On days 2, 3, 5, 8, and 11, 0.1 ml of media was removed from each well and 0.1 ml of DMEM containing HAT was added. After 8 days culture supernatants were screened for antibodies reacting with SQE and not SQA by ELISA on PVDF plates as described below. Cells from culture supernatants that were positive were expanded and then cloned twice by limiting dilution.

Example 3

ELISA for Testing Serum for Antibodies to SQE Using Polystyrene (PS) Plates

Solid-phase ELISAs were performed as described previously with minor modifications (Alving et al., 1996). For the initial serum screen assays, 10 µg of SQE or SQA in 50 µl of ethanol was placed in PS "U" bottom plates. The plates were placed overnight in a biological safety cabinet to allow the ethanol to evaporate. The plates were blocked with 0.25 ml of PBS-0.3% gelatin for 2 h. After removal of the blocking buffer, 50 µl/well of serum diluted in PBS-0.3% gelatin was added in triplicate. The plates were incubated at 4° C. overnight. The plates were then washed 3 times with PBS using a plate washer (Skatron Inc., Sterling, Va.).

Peroxidase-labeled goat IgM (μ chain specific) were diluted 1000-fold in PBS-0.3% gelatin and 50 μl/well was added to the plates. Following incubation at room temperature for 1 h, the plates were washed 3 times with PBS. ABTS substrate (50 μl/well) was added and the plates were incubated for 1 h at room temperature in the dark. The absorbance at 405 nm was quantified using a UVmax Kinetic Microplate Reader (Molecular Devices, Palo Alto, Calif.). Assays were conducted in triplicate. Assay background was determined by incubation with wells lacking antigen. Background was subtracted from experimental values. Endpoint antibody titers were selected as the dilution at which the absorbance was twice background.

Example 4

ELISA for Testing Culture Supernatants for Antibodies to SQE Using PS Plates

For assay of culture supernatants of monoclonal antibodies, PS flat bottom plates were used. The assay was similar to that described above for the "U" bottom plates with the following changes. 1) The assay volumes of coating antigen, primary and secondary antibodies and substrate was increased from 50 μl to 100 μl; 2) SQE and SQA were dissolved in isopropanol; 3) Incubation of with culture supernatants was for 1 h at room temperature instead of overnight at 4° C. These changes gave less background and somewhat greater reproducibility among triplicate determinations when compared to ELISA on PS "U" bottom plates. However, better results were obtained using PVDF membranes.

Example 5

ELISA for Antibodies to SQE Using PVDF Plates

The assay for antibodies to SQE was modified from the method described for detecting antibodies to cholesterol by Dijkstra et al. (1996). 0.1 ml of SQE or SQA, as appropriate, dissolved in isopropanol were placed in each well and the plate was placed overnight in a biological safety cabinet to allow the isopropanol to evaporate. The wells were blocked with PBS-4% FBS, pH 7.4, (0.3 ml/well) and incubated at room temperature for at least 1 hr. After removal of the blocking buffer, 0.1 ml of culture supernatant (either undiluted or diluted in PBS-4% FBS) was added to each well. The plate was covered with seal plate adhesive film and placed on a orbital shaker set at 1,500 rpm for 1 hr. The plates were then washed 4 times with PBS-4% FBS. Sufficient PBS-4% FBS was added to each well until the air bubble floated off the PVDF membrane. Peroxidase-linked goat anti-mouse IgG or IgM was diluted 1 to 1000 in PBS-4% FBS and 0.1 ml was added to each well. The plates were covered with seal plate adhesive film and placed on the shaker as described above. The plates were washed 4 times with PBS as described above. ABTS substrate (0.15 ml/well) was added and the plates were covered with seal plate adhesive film. They were placed on the shaker, covered with aluminum foil, and shaken at 1,500 rpm. After 1 hr, 0.05 ml was transferred from each well and placed in a corresponding well of 96 well "U" bottom plate. The absorbance was read at 405 nm using an ELISA plate reader.

Example 6

ELISA Using L(SQE), L(SQA) and L as Capture Antigens

ELISAs using liposomes as capture antigens were performed using "U" bottom PS plates. L(SQE), L(SQA), or L, as appropriate, were diluted to 660 nmol/ml in PBS (equivalent to 10 μg SQE). Fifty μl (33 nmol) were placed in each well. The plate was placed in a biological safety cabinet overnight. The plates containing the dried film of liposomes were processed by ELISA as described in section 2.7. For serum assays, the plates containing diluted serum were incubated overnight at 4° C. For assays using diluted supernatants from the monoclonal antibodies, the plates were incubated 1 h at room temperature.

Example 7

Induction and Reactivity of Polyclonal Antisera with SQE by ELISA

Figure 2:
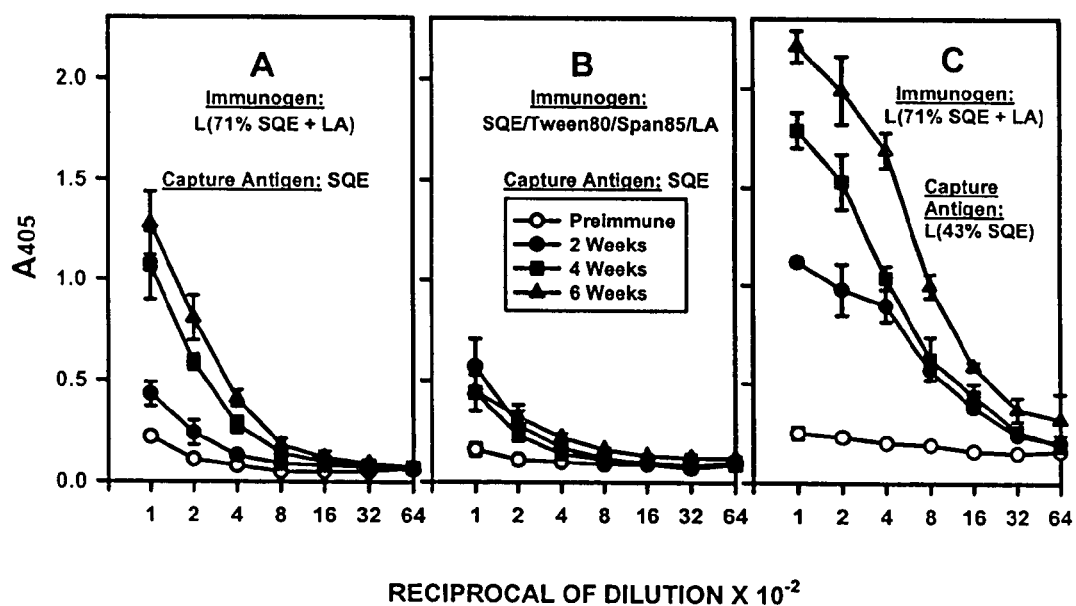

Sera from immunized mice were tested by ELISA for the presence of anti-SQE antibodies using SQE as the capture antigen. Among the eight immunization strategies employed (see Materials and Methods, and summary in Table I), only two groups exhibited increased IgM binding activity after injection of the antigen when compared to the preimmunization serum (group 4, FIG. 2A; group 6, FIG. 2B). None of the groups developed IgG binding activity after immunization (data not shown). Mice injected with liposomes containing lipid A and 71% SQE [L(71% SQE+LA)] (group 4, see Table I) showed progressively increased IgM titers with time when compared to the pre-immunization bleeding (FIG. 2A). The animals were immunized every 2 weeks, and even at 2 weeks after a single injection, an increased IgM titer was evident. To a much lesser extent one of the SQE emulsion groups (group 6, see Table I) also developed increased titers when compared to the pre-immune sera, but even after multiple injections there was no progressive increase in the antibody titer (FIG. 2B). Because of this, in all further experiments sera from animals immunized with L(71% SQE+LA) was used.

Figure 3:
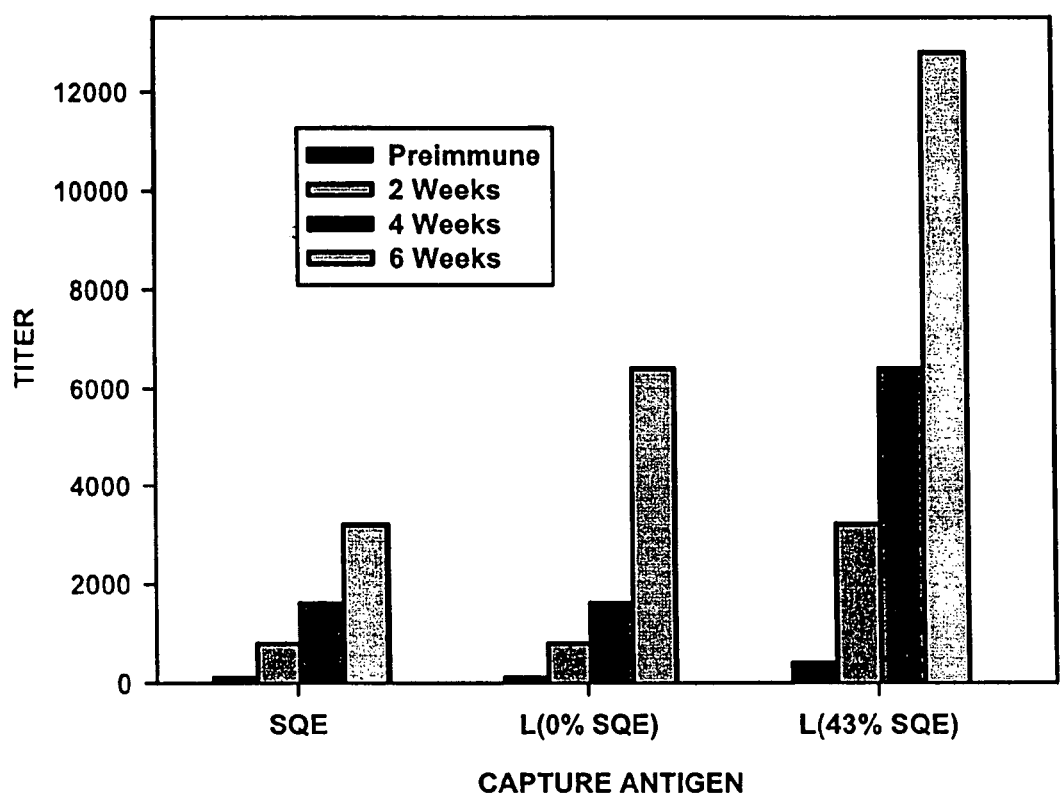

Using an alternative capture antigen in the ELISA, namely liposomes containing SQE an even higher resolution of positive results was observed when compared to the results obtained with SQE alone (FIG. 3A) as a capture antigen. However, as shown in FIG. 3, after immunization with liposomes containing SQE and lipid A, the antisera reacted not only with SQE alone but also with liposomes lacking SQE, albeit to a much lesser extent than with liposomes containing SQE. This latter observation is consistent with previous reports that antibodies to phospholipids are also induced when liposomal lipid A, or even lipid A alone, is used as an adjuvant (Schuster et al., 1979; Banerji et al., 1981; Alving, 1986).

The above data suggested that antibodies that could react with SQE were induced in mice by immunization with certain formulations that contained SQE. However, when another oil molecule, SQA, the fully hydrogenated form of SQE, was substituted for SQE as a capture antigen in the ELISA, the polyclonal antiserum to SQE reacted equally well with either SQE or SQA (data not shown). This apparent lack of monospecific binding to SQE could have been due either to extensive cross-reactivity of anti-SQE antibodies with SQA, or to a mixed population of antibodies, some of which cross-reacted with SQA and some of which did not. The possibility of nonspecific binding of IgM antibodies also existed. Because of this, we decided to try to produce monoclonal antibodies that could differentiate between SQE and SQA as antigens. In the course of this work, as shown below, we also refined the ELISA assay to minimize nonspecific effects and increase resolution.

Example 8

Development of Monoclonal Antibodies to SQE

Figure 4:
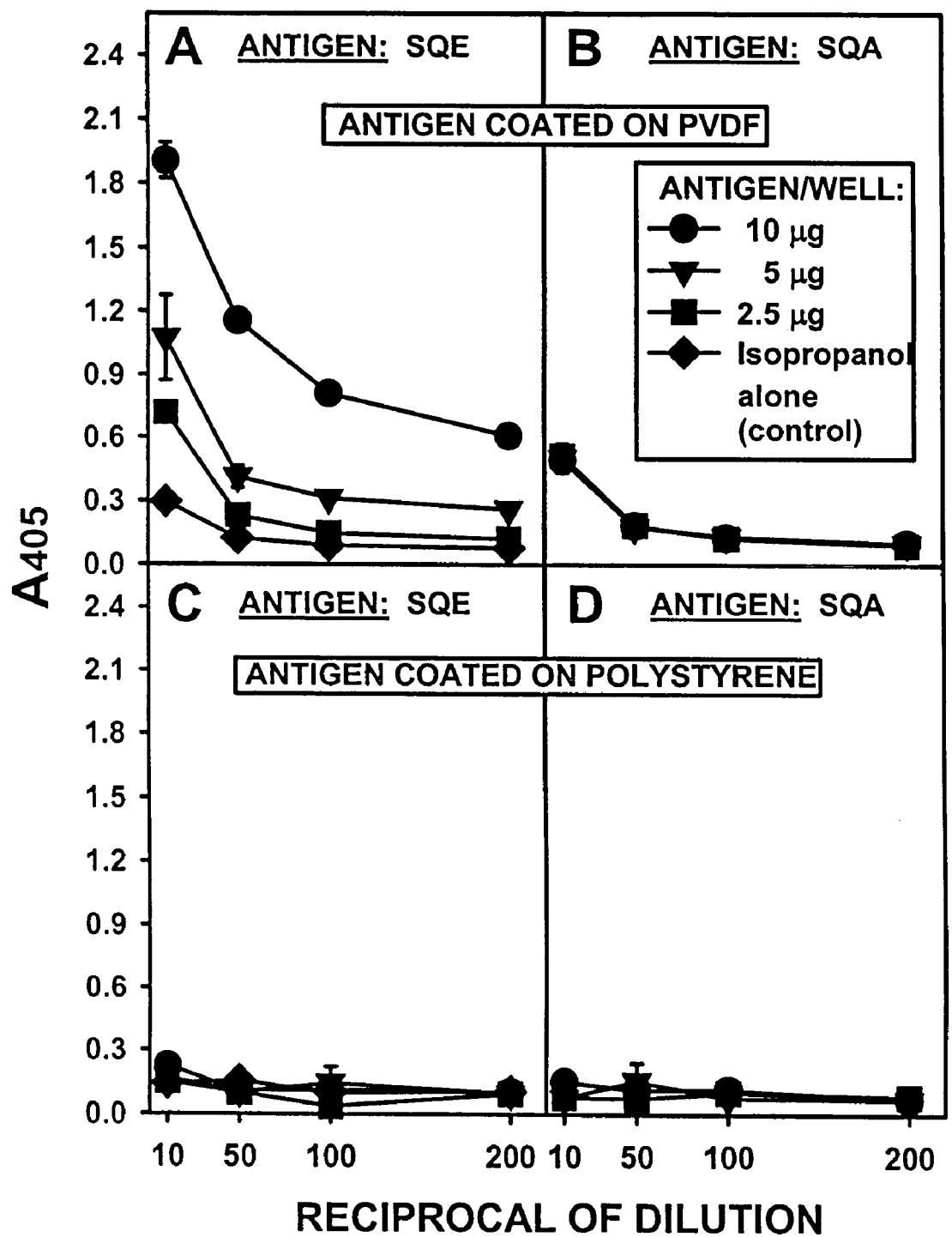

To minimize experimental variation and nonspecific effects observed after coating of hydrophobic antigens on polystyrene microtiter wells, we examined the possible benefits of coating the capture antigens on hydrophobic membranes consisting of polyvinylidene fluoride (PVDF), as described by Aniagolu et al. (1995). As shown in FIGS. 4A and B, when culture supernatants were assayed with PVDF membranes, an IgM anti-SQE mAb was identified that exhibited strong dose-dependent binding to SQE, but displayed little or no cross-reactivity to SQA. When the antigens were coated on flat bottom PS microtiter wells instead of PVDF membranes, the same anti-SQE mAb showed a complete lack of reactivity with either SQE or SQA (FIGS. 4C and D).

Figure 5:
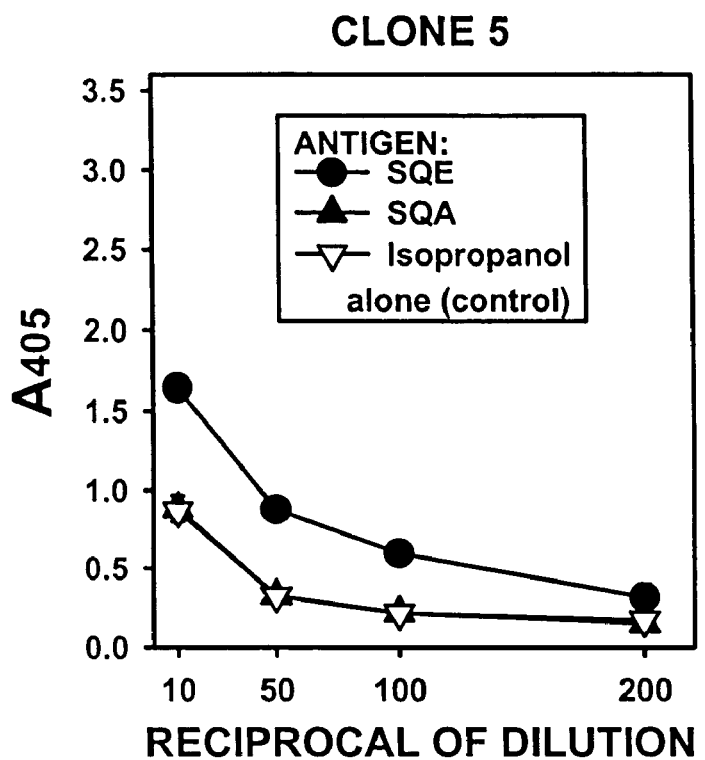
Figure 6:
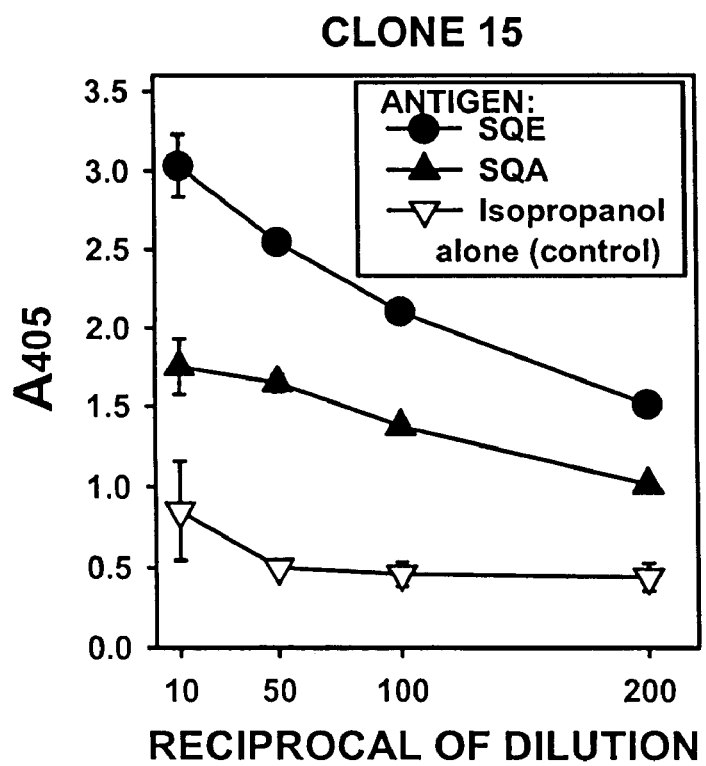

Additional clones of anti-SQE mAbs were also produced which, when tested with the PVDF membrane assay, either showed striking specificity for SQE (clone 5, FIG. 5), or reactivity with both SQE and SQA (clone 15, FIG. 6). These data demonstrate that mAbs can be identified that differentiate free SQE from free SQA by ELISA, particularly when the antigens are coated on PVDF membranes.

Example 9

Figure 7:
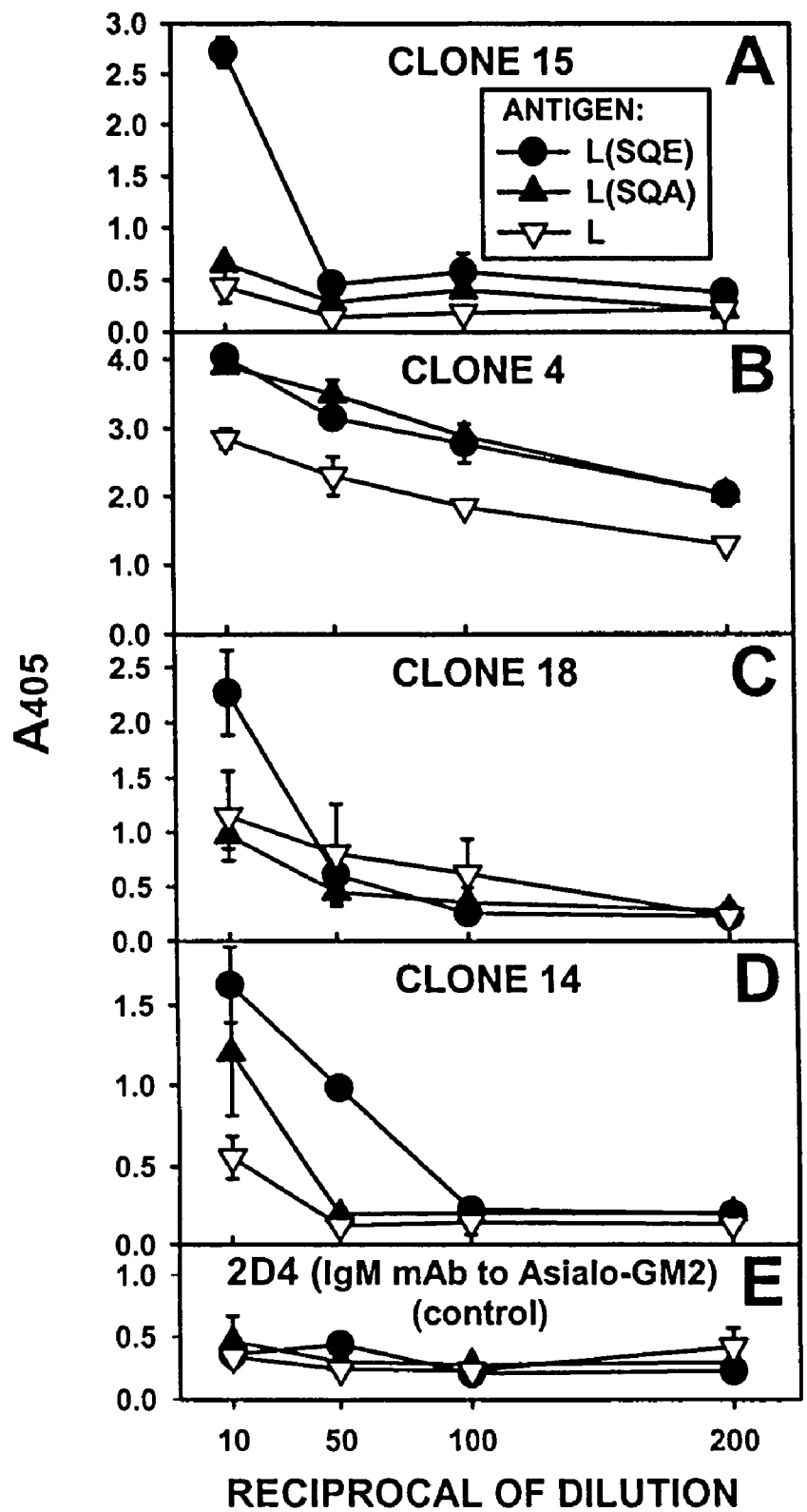

Evaluation of the Specificity of mAbs for Reactivity with a Capture Antigen Consisting of Liposomes Containing SQE or SQA The original immunizing antigen consisted of liposomes containing SQE+LA. FIG. 7 illustrates the results of ELISAs in which PS plates were coated with liposomes containing or lacking SQE or SQA. An irrelevant IgM mAb (anti-asialoG$_{M2}$) is shown as a negative control (FIG. 7E). When analyzed for reactivity with liposomes containing SQE [L(SQE)], liposomes containing SQA [L(SQA)], or liposomes lacking both SQE and SQA [L], four different patterns of specificity for L(SQE), L(SQA), and L alone were observed, as derived from FIG. 7 and summarized in Table II. It is noteworthy that we have never obtained a mAb that bound more strongly to SQA than to SQE. This is in keeping with the primary specificity of the antibodies for liposomal SQE.

Evaluation of the Specificity of Polyclonal Antiserum for SQE and SQA on PVDF Membranes.

Figure 8:
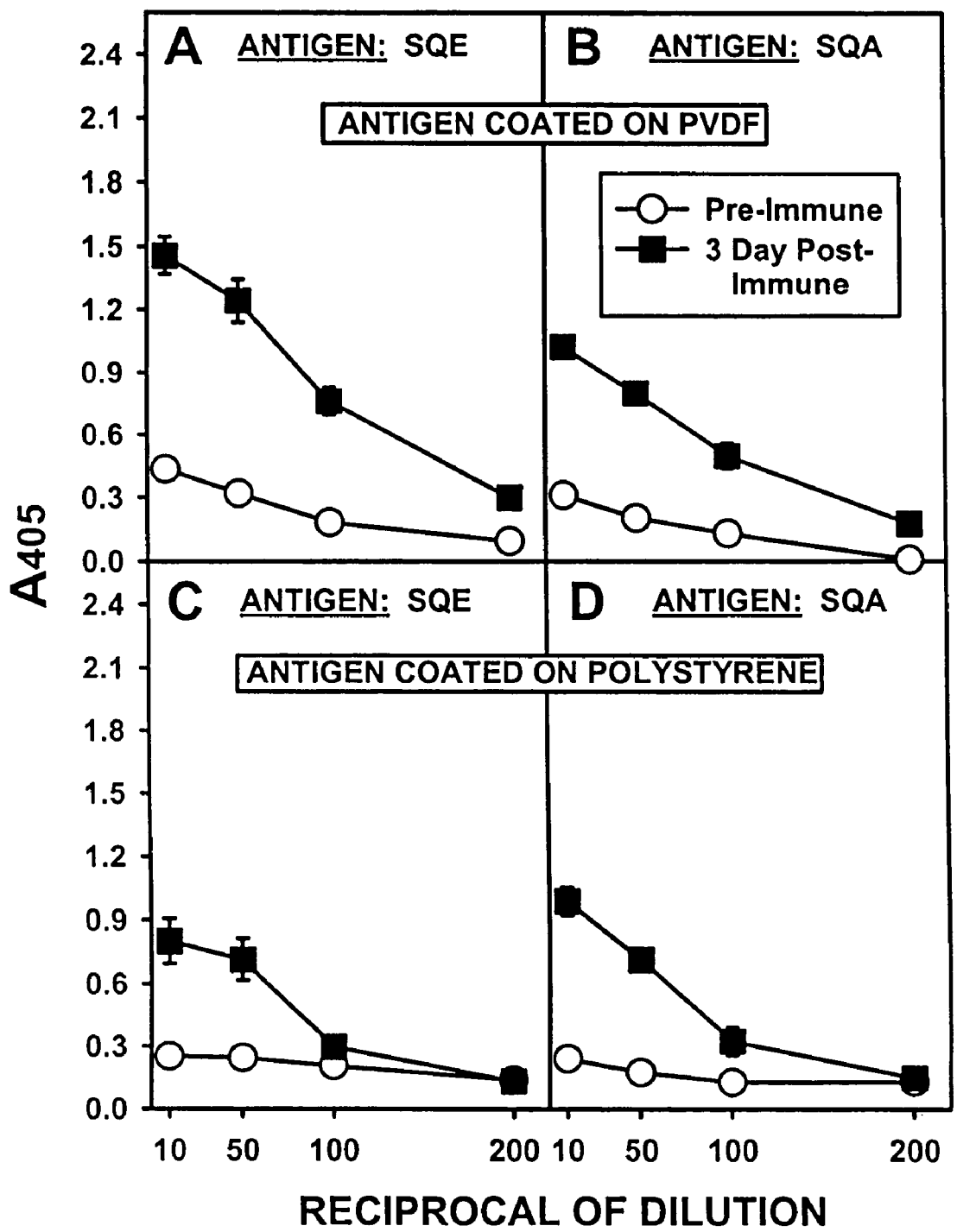

The above studies demonstrate that immunization with SQE induces a mixed population of anti-SQE antibodies that includes some that do not cross-react and some that do cross-react with SQA. In view of this, polyclonal anti-SQE antiserum would be expected to exhibit both SQE reactivity and SQA cross-reactivity on PVDF membranes. As shown in FIG. 8, reactivity with both antigens was observed with polyclonal anti-SQE antiserum.

To demonstrate that specific antibodies to SQE actually do exist, we created mAbs that were selected for the ability to bind to SQE but had a relative inability to bind to SQA, as determined by ELISA with hydrophobic PVDF membranes. Monoclonal antibodies were successfully created that specifically bound to SQE but to a lesser extent, or not at all, to SQA. However, numerous anti-SQE mAbs were also created that cross-reacted strongly with SQA. It is concluded that specific differentiation of SQE from SQA demonstrates that the unsaturated bonds of SQE can play a major role in the specificity of the antibodies, and such antibodies therefore have a distinctive conformational specificity. However, the extensive cross-reactivity of numerous clones of anti-SQE antibodies with SQA also demonstrates that the unsaturated bonds are not the sole determinant of specificity.

Example 10

We have demonstrated in this study that polyclonal and monoclonal antibodies that bind to SQE can be developed after immunization of mice with liposomes containing 71% SQE and lipid A. Other methods of immunization, including immunizing with liposomes containing 43% SQE or with a variety of SQE-containing emulsions, were either completely ineffective, or considerably less effective, as immunogens. The strategy of utilizing liposomes containing 71% SQE and lipid A as an immunogen was modeled after similar success in the induction of antibodies to cholesterol by immunizing with liposomes containing 71% cholesterol and lipid A (Swartz et al., 1988; Alving and Swartz, 1991; Dijkstra et al., 1996). Although we have previously found that simple injection of silicone oil into mice can also cause the induction of antibodies to cholesterol (Alving et al., 1996), injection of non-emulsified SQE oil mixed with lipid A did not result in the induction of antibodies to SQE (group 2, Table I). Among four emulsions containing SQE and lipid A as components, only one (group 6, Table I) induced any immune response to SQE, and this was quite weak even after multiple injections (FIG. 2B). From these data we conclude that SQE is a very poor antigen when used either as an oil or an emulsion, even when lipid A, a potent adjuvant for inducing antibodies to lipids, is included in the immunizing formulation.

The results in the present study are consistent with the concept of induction of anti-liposome mAb antibodies having specificities that include both liposomal phospholipid as well as SQE in the antigen binding site of the antibody (FIGS. 7B and C; Table II). However, as with the anti-cholesterol mAbs, anti-SQE clones were also obtained that did not react with liposomal phospholipid (FIGS. 7A and D; Table II).

TABLE II

Monoclonal Antibody Specificities Obtained After Injection of Liposomes Containing Lipid A and SQE

| Clone No. | Binding Specificity* | | |
|---|---|---|---|
| | SQE | SQA | Liposomal phospholipid |
| 15 | + | − | − |
| 4 | + | + | + |
| 18 | + | − | + |
| 14 | + | + | − |

*Based on data from Figure 7.

Example 11

The extreme hydrophobicity of SQE raises an important theoretical problem in demonstrating specificity of antibodies because polyclonal antiserum raised by immunization with SQE shows considerable reactivity with SQA (FIG. 8). Based on serum data alone, it was therefore initially impossible to determine whether the apparent antibody activity in the antiserum is specific to SQE, or if the immunoglobulins are simply nonspecifically binding hydrophobically both to SQE and SQA. Our initial experiments using PS microtiter plates did indeed demonstrate nonspecific hydrophobic binding of IgM molecules to both SQE and SQA, and other alkanes (data not shown). However, this problem was solved by coating the antigens on hydrophobic PVDF membranes, as described by Aniagolu et al. (1995). Although commercially-available PVDF membranes also present the problem that they are physically located in PS microtiter wells, they apparently do have the salutary effect of blocking most or all of the nonspecific hydrophobic binding sites of the alkane molecules.

Example 12

Culture supernatants containing monoclonal antibodies (mAbs) to SQE were grown in Dubbelco's modified Eagle's medium as described (Matyas) Mice were injected with liposomes containing 71 mol percent SQE and lipid A, intrapertioneally as described (matyas). Anti-SQE positive serum was obtained by terminal bleeding three days after immunization. The serum was aliquoted and frozen at −20° C. The experiments described in this paper used several different lots of monoclonal supernatants and anti-SQE serum.

Example 13

ELISA Assay on PVDF Plates

The ELISA assay in plates containing PVDF membranes were conducted as described (matyas). Briefly, SQE was diluted in isopropanol and placed in the wells of the plate. After drying overnight, the wells were blocked with PBS-4% FBS, pH 7.4, for 2 h. Serum and supernatants containing monoclonal antibodies to SQE were diluted in PBS-4% FBS and 0.1 ml was placed in a well. Following incubation for 1 h, the plate was washed four times with PBS-4% FBS by hand using a 25 ml pipet. 0.1 ml of peroxidase-linked sheep anti-mouse IgM diluted 1:1000 in PBS-4% FBS was added to each well. The plate was incubated for 1 h and then washed 4 times with PBS by hand. 0.15 ml of ABTS substrate was added to each well and the plates were incubated for 1 h. 0.1 ml/well was transferred to an Immulon 2 U bottom plate and the absorbance was read at 405 nm with a Uvmax Kinetic Microplate Reader (Molecular Devices, Palo Alto, Calif.). In some experiments PVDF plates were washed 4 times with 0.5 ml of PBS/well with an ELISA plate washer (Skatron, Sterling, Va.). The vacuum probes of the washer were positioned just above the PVDF membrane.

Example 14

ELISA Assay on Polystyrene Plates

The ELISA assay for polystyrene plates was performed as described (Matyas). The assay for polystryrene tissue culture U bottom plates is described in detail. SQE was diluted in isopropanol (1 µmol/ml; 24 µl SQE/50 ml) and 0.1 ml was placed in each well. Control wells were isopropanol alone. The plates were placed in a biological safety cabinet and incubated overnight to allow the isopropanol to evaporate. PBS-4% FBS, pH 7.4 was added to each well (0.3 ml/well) to block unbound binding sites. After incubation at room temperature for 2 h, the plates were dumped and tapped on paper towel to removed the blocked. Culture supernatants containing monoclonal antibodies to SQE or mouse serum was diluted in PBS-2% BSA and added to the plates in triplicate. Following incubation for 1 h at room temperature, the plates were washed 4 times with 0.5 ml of PBS/well using a Skatron plate washer. Peroxidase-linked sheep anti-mouse IgM was diluted 1:1000 in PBS-4% FBS and 0.1 ml was added to each well of the plate. The plates were incubated 1 h at room temperature and washed 4 times with PBS. ABTS substrate (0.1 ml/well) and the plates were incubated at room temperature for 1 h. Absorbance was read at 405 nm.

Example 15

Effect of Polystyrene Plate Type on the Measurement of Antibodies to SQE

Figure 9:
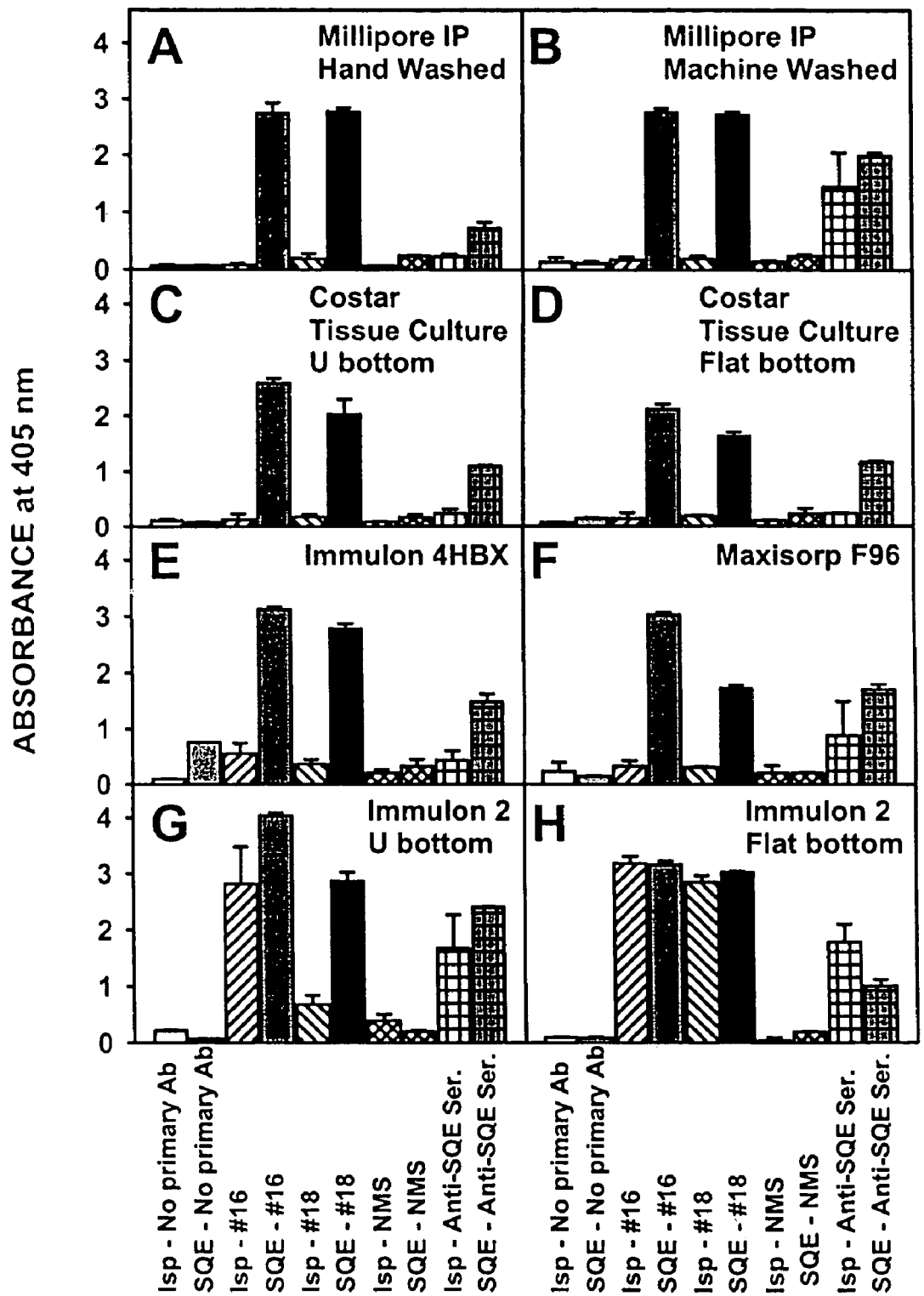

Seven different plates coated with SQE as an antigen were compared for their ability to detect monoclonal antibodies and serum antibodies to SQE. Hand washed Millipore IP plates had low background (isopropanol-treated wells) and high anti-SQE absorbances for the mAbs, but low absorbances to SQE-coated wells were obtained for anti-SQE serum (FIG. 9A). When the Millipore IP plates were washed with an ELISA plate washer, the background absorbances for the anti-SQE serum significantly increased (FIG. 9B). Immulon 2 U and flat bottom plates had very high background absorbances for the mAbs and the anti-SQE serum (FIGS. 9G, H). Immulon 4HBX had elevated absorbances for SQE-coated wells that were not incubated with primary antibody (FIG. 9E). Maxisorp F96 plates had elevated background absorbances with anti-SQE serum. Costar U and flat-bottom tissue culture plates had low background absorbances and high absorbances for SQE-coated wells with both the mAbs and anti-SQE serum (FIGS. 9C, D). There were no real differences in ELISA values observed between the U bottom and flat bottom Costar tissue culture plates. The Costar U bottom plate was chosen for the assay of antibodies to SQE.

Example 16

Figure 10:
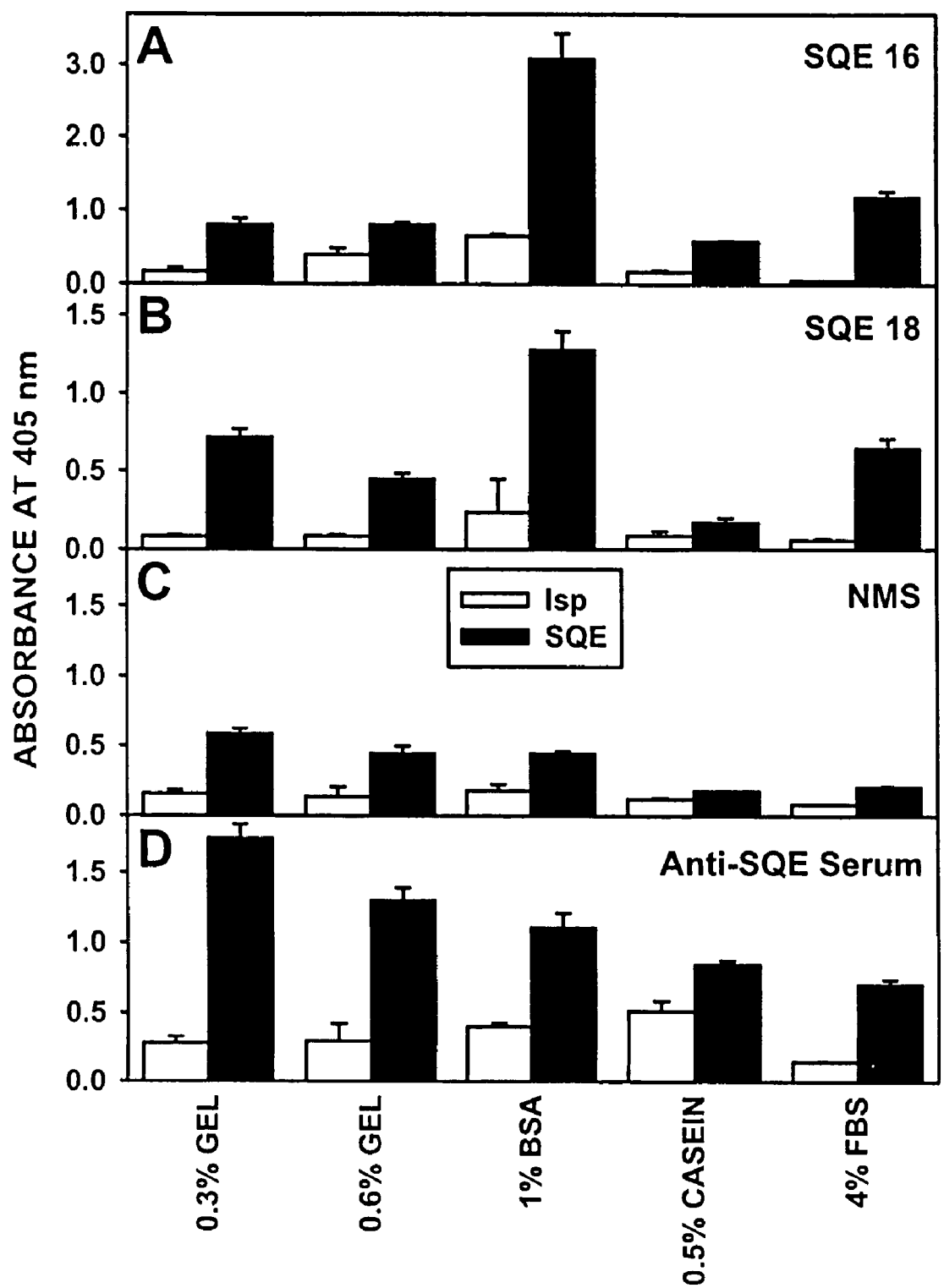
Figure 11:
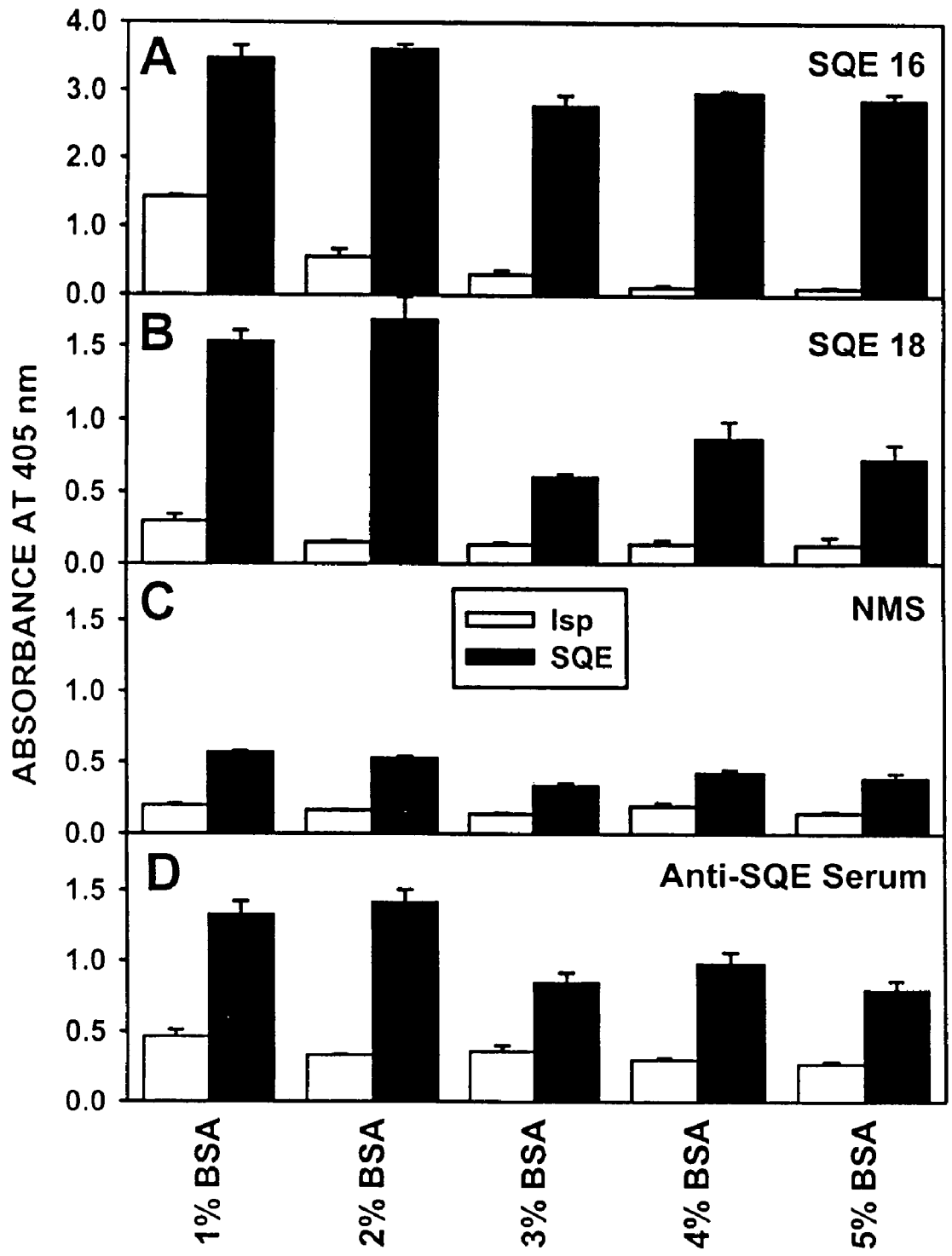

Standardization of the ELISA Assay for Anti-SQE Antibodies on Costar U Bottom Tissue Culture Plates The plates were tested with various blocker/diluents in order to minimize background and maximize antibody binding to SQE. PBS-0.5% casein effectively abolished the binding of the mAbs to SQE (FIGS. 10A, B) and elevated the background with the anti-SQE serum (FIG. 11D). PBS-0.3% gelatin and PBS-0.6% gelatin inhibited the binding of the mAbs to SQE-coated wells (FIGS. 10A, B). In addition, when gelatin was used as a blocker/diluent, the results from experiment to experiment were highly variable. When PBS-1% BSA was used as a blocker/diluent, absorbances increased over 2-fold for the mAbs on SQE-coated wells compared to similar wells using PBS-4% FBS as a blocker/diluent (FIGS. 10A, B). Background absorbances with PBS-1% BSA were similarly increased approximately 2-fold for both the mAbs, normal mouse and anti-SQE serum (FIG. 10). Various concentration of BSA were tested to determine if the background could be reduced. mAbs and anti-SQE serum had high absorbances for SQE-coated wells using PBS-1% and 2% BSA as blockers/dilutents (FIG. 11). BSA concentrations greater than 2% caused significant reductions in the absorbances of SQE #18 (FIG. 11B) and anti-SQE serum (FIG. 11D). Background absorbances for isopropanol-treated wells were greatly reduced by increasing the BSA from 1% to 2%, but did were not dramatically reduce further with increasing concentrations of BSA (FIG. 11). PBS-2% BSA was chosen as the blocker/diluent.

Figure 12:
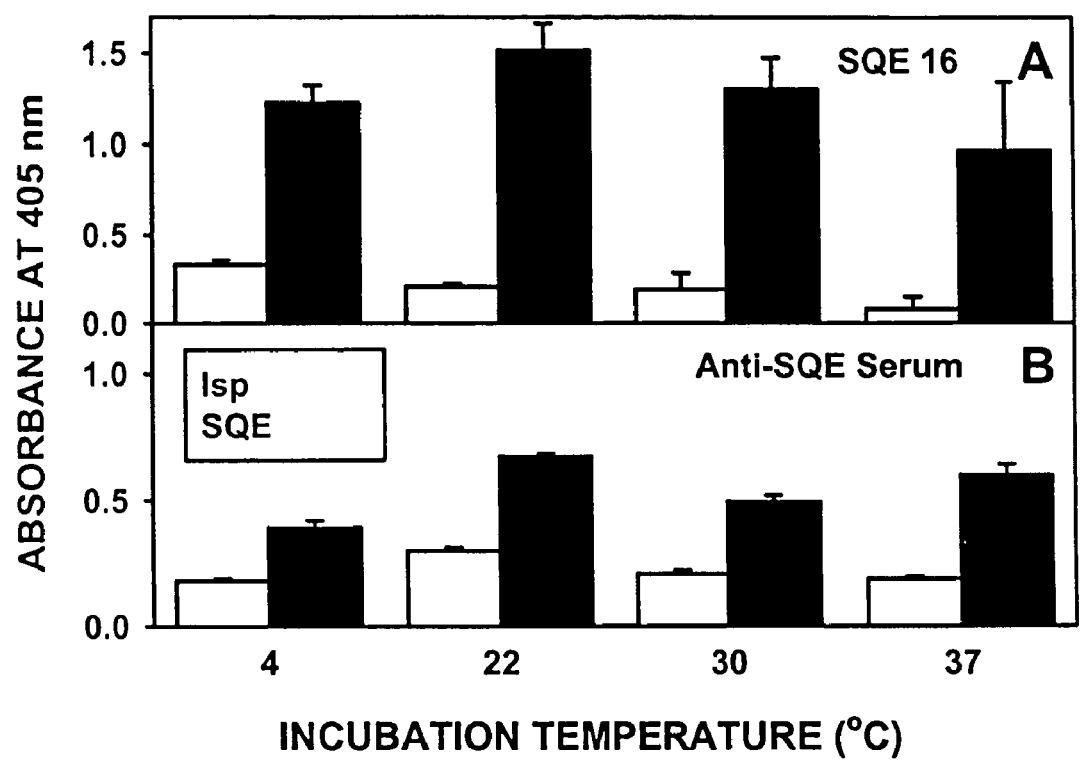

The optimal incubation temperature was investigated. The binding of clone SQE #16 was independent of the incubation temperature (FIG. 12A). Maximal binding of anti-SQE serum to SQE-coated wells occurred at temperatures above 4° C. (FIG. 12B). Background binding of anti-SQE serum to isopropanol-treated wells was relatively independent of temperature. There was a slight increase in binding to isopropanol-treated wells at 22° C. Since binding was basically independent of temperature, room temperature was chosen for the standard assay.

A comparison of the time required for primary antibody binding to SQE-coated wells indicated that overnight incubation did not increase the binding of clone SQE #16 to SQE-coated wells (FIG. 13A). There was increased binding of anti-SQE serum to SQE-coated wells with overnight incubation, but this was mostly offset by and an increase in background binding to isopropanol-treated wells (FIG. 13B). One hr was chosen as the incubation time for primary antibody. Similarly, there was no difference between incubating with secondary antibody for 1 or 2 hr for both clone SQE #16 and anti-SQE serum (FIG. 14). Consequently, 1 hr was chosen as the incubation for secondary antibody.

The binding of mAbs SQE #14 and SQE #16 was dependent upon the amount of SQE added to the wells (FIG. 15A, B). Maximal binding was observed from 10 to 25 nmol of SQE. Maximal absorbances for anti-SQE serum were obtained from 7.5 to 100 nmol of SQE. SQE amounts above or below those amounts had decreased absorbances. Control mouse IgM monoclonal antibody did not bind to SQE at any amount coated on the plate (FIG. 15A). Ten nmol of SQE was chosen as the preferred amount for the standard assay.

Example 17

Conditions for the Standard Assay for Measuring Antibodies to SQE

Based on the results described above, the following conditions were adopted as the standard assay conditions:

1. Costar 96 well "U" bottom sterile tissue culture plates were chosen.

2. A SQE concentration of 10 nmol SQE/well in 0.1 ml of isopropanol was chosen. The isopropanol was allowed to evaporate over night in a biological safety cabinet with the air turned-on.

3. The plates were blocked with 0.3 ml/well of PBS-2% BSA, pH 7.4 for 2 hr at room temperature.

4. Mouse serum or monoclonal antibodies are diluted in PBS-2% BSA.

5. The plates are dumped and tapped on paper towels. 0.1 ml/well of diluted serum or monoclonal antibody was added to the plate. The plates were covered and incubated at room temperature for 1 hr.

6. The plates were washed 4 times with PBS, pH 7.4 with 0.5 ml/well.

7. Peroxidase-linked sheep anti-mouse IgM was diluted 1:1000 in PBS-2% BSA and 0.1 ml was added to each well. The plates are covered and incubated at room temperature for 1 hr.

8. The plates were washed 4 times with PBS, pH 7.4 at 0.5 ml/well.

9. 0.1 ml of ABTS substrate was added to each well. The plates were covered with foil and incubated at room temperature for 1 hr.

10. The absorbance was read at 405 nm.

Example 18

Reproducibility of the Assay

Several different lots of Costar U bottom tissue culture plates were tested under the standard assay conditions. There was no difference among the absorbances obtained with the mAbs on the different lots of plates (FIGS. 16A, B). Slight differences in absorbances were observed with different lots of plates with anti-SQE serum on SQE-coated wells (FIG. 17C). Background absorbances were the same on the different lots of plates for both the monoclonal antibodies and the anti-SQE serum. The assay was highly reproducible from day to day both with the monoclonal antibodies (FIG. 17A) and with anti-SQE serum (FIG. 17B).

Example 19

Detection of Antibodies to Squalene in Human Sera

Squalene and squalane oils were purchased from Sigma-Aldrich Chemical Company, St. Louis, Mo. Isopropanol and casein were purchased from J. T. Baker, Phillipsburg, N.J. Gelatin was from BioRad Laboratories, Richmond, Calif. Flat and U bottom tissue culture plates were from Costar-Corning, Corning, N.Y. Affinity purified and adsorbed peroxidase-linked sheep anti-human IgG and IgM was from The Binding Site, San Diego, Calif. ABTS substrate was purchased from Kirkegaard and Perry Laboratories, Gaithersburg, Md. Human serum samples were obtained under IRB approved protocol from Phillip Pittman at the United States Army Medical Research Institute of Infectious Disease, Frederick, Md.

ELISA Assay

Squalene was diluted in isopropanol to 0.2 µmol/ml (9.6 µl squalene/100 ml) and 0.1 ml was placed in each well. Control wells contained isopropanol alone. The plates were placed in a biological safety cabinet and incubated overnight to allow the isopropanol to evaporate. PBS-0.5% casein, pH 7.4, was added to each well (0.3 ml/well). After incubation at room temperature for 2 h, the plates were dumped and tapped on a paper towel to removed the blocking buffer. Serum samples were diluted in PBS-0.5% casein and added to the plates in triplicate. Following overnight incubation at room temperature, the plates were washed 4 times with 0.5 ml of PBS/well using a MAP-C ELISA workstation (Titertek, Huntsville, Ala.). Peroxidase-linked sheep anti-human IgG and IgM was diluted 1:1000 in PBS-0.5% casein and 0.1 ml was added to each well of the plate. The plates were incubated 1 h at room temperature and washed 4 times with PBS. ABTS substrate (0.1 ml/well) and the plates were incubated at room temperature for 1 h. Absorbance was read at 405 nm.

Serum Anti-Squalene Grading Criteria

POSITIVE—The absorbance for the squalene-coated wells was at least 2.5 times that of isopropanol-treated wells and 10 times the absorbance for squalene-coated wells that were not incubated with primary antibody.

INCONCLUSIVE—(high background) The absorbance for isopropanol-treated wells was at least 5 times the absorbance of isopropanol-treated wells that were not incubated with primary antibody and the absorbance for the squalene-coated wells was at least 10 times the absorbance for squalene-coated wells that were not incubated with primary antibody.

NEGATIVE—The absorbances failed to meet the above criteria.

Summary

A. 4.1% of the serum samples (8 of 197) were positive for IgG antibodies to squalene.

B. 95.9% of the serum samples (189 of 197) were negative for IgG antibodies to squalene.

C. 10.2% of the serum samples (20 of 197) were positive for IgM antibodies to squalene.

D. 14.2% of the serum samples (28 of 197) were inconclusive for IgM antibodies to squalene. These sera had high background binding to isopropanol-treated wells.

E. 75.6% of the serum samples (149 of 197) were negative for IgM antibodies to squalene.

F. Most of the positive anti-squalene samples had endpoint titers of 100-200.

The results for these experiments are shown graphically in FIGS. 18-22.

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings.

The invention claimed is:

1. An assay method for detecting the presence of squalene antibodies comprising the steps of providing a solid support immobilized with squalene thereon, adding bovine serum albumin as a blocking agent to said solid support, and contacting the immobilized squalene with a serum sample containing squalene antibodies to form an antibody complex, and binding the antibody complex with a labeled ligand for detecting the presence of squalene antibodies in said serum sample.

2. The method of claim 1 wherein the method further comprises using a monoclonal antibody to specifically bind to any squalene antibodies present in the serum.

3. A method for detecting squalene antibodies in serum comprising the steps of immobilizing squalene on a solid support, contacting the immobilized squalene with a serum sample containing squalene antibodies to form an antibody complex, and binding the antibody complex with a ligand in which the ligand is an antibody capable of capturing said antibody complex.

4. A method for detecting the presence of squalene antibodies capable of specific binding with squalene, comprising:
   providing a solid support suitable for allowing specific binding of squalene with squalene antibodies;
   immobilizing squalene on the solid support;
   allowing squalene antibodies to specifically bind to the immobilized squalene to form a specific antibody complex;
   contacting the antibody complex with an indicator agent specifically binds to the complex; and
   detecting the indicator agent.

5. The method of claim 4 further comprising the step of blocking the immobilized squalene with a blocking agent to reduce background interference with antibody binding to the immobilized squalene.

6. The method of claim 4 where the detection is part of an ELISA protocol.

* * * * *